(12) United States Patent
Bucove et al.

(10) Patent No.: US 8,738,160 B2
(45) Date of Patent: May 27, 2014

(54) APPARATUS AND METHOD FOR PLANT METABOLISM MANIPULATION USING SPECTRAL OUTPUT

(76) Inventors: Jeffery Bucove, Victoria (CA); David A. Hillstrom, III, Clifton Forge, VA (US)

( * ) Notice: Subject to any disclaimer, the term of this patent is extended or adjusted under 35 U.S.C. 154(b) by 357 days.

(21) Appl. No.: 13/055,461

(22) PCT Filed: Jul. 25, 2009

(86) PCT No.: PCT/IB2009/053254
§ 371 (c)(1),
(2), (4) Date: Jan. 23, 2011

(87) PCT Pub. No.: WO2010/010540
PCT Pub. Date: Jan. 28, 2010

(65) Prior Publication Data
US 2011/0125296 A1    May 26, 2011

Related U.S. Application Data

(60) Provisional application No. 61/083,886, filed on Jul. 25, 2008.

(51) Int. Cl.
*G06F 17/00* (2006.01)
*A01G 7/04* (2006.01)
*A01H 3/00* (2006.01)

(52) U.S. Cl.
CPC .. *A01G 7/045* (2013.01); *A01H 3/00* (2013.01)
USPC ......... 700/90; 700/266; 47/58.1 LS; 315/294; 315/152; 435/7.2; 435/34; 435/29

(58) Field of Classification Search
USPC .................... 700/90, 276; 435/34, 7.2, 29; 47/58.1 LS; 315/294, 152
See application file for complete search history.

(56) References Cited

U.S. PATENT DOCUMENTS 5,012,609 A * 5/1991 Ignatius et al. ............ 47/1.01 R
5,506,117 A * 4/1996 Andrews et al. ................ 435/29
5,739,305 A * 4/1998 Cubicciotti .................. 536/23.1
(Continued)

OTHER PUBLICATIONS

Folta, K.M. and Childers, K.S., "Light as a Growth Regulator: Controlling Plant Biology with Narrow-Bandwidth Solid-State Lighting Systems", Dec. 2008, HortScience, vol. 43, Iss. 7.*

(Continued)

*Primary Examiner* — Mohammad Ali
*Assistant Examiner* — Kelvin Booker
(74) *Attorney, Agent, or Firm* — Davis & Bujold, PLLC; Michael J. Bujold

(57) ABSTRACT

A method and apparatus for metabolism manipulation of life forms using spectral output which comprises at least one array of LED light sources which have metabolic manipulating spectral emissions. The array sends one or more environmental signals selected from the group consisting of day/night cycles, seasonal cycles, competitive signals and harsh condition preparedness. A remotely programmable microcontroller is operatively connected to the at least one array for controlling the spectral emissions in a desired manner. The microcontroller selectively sending on commands, off commands and intensity commands to the at least one array. The method and apparatus include software for driving the microcontroller and the software is stored in a memory. A power source is operatively connected to the at least one array of LED light sources, and a graphic user interface facilitates inputting information, by an operator.

24 Claims, 23 Drawing Sheets

(56) References Cited

U.S. PATENT DOCUMENTS

| | | | | |
|---|---|---|---|---|
| 5,756,296 | A * | 5/1998 | Cubicciotti | 435/6.11 |
| 5,784,162 | A * | 7/1998 | Cabib et al. | 356/456 |
| 6,100,026 | A * | 8/2000 | Nova et al. | 506/41 |
| 6,319,668 | B1 * | 11/2001 | Nova et al. | 506/28 |
| 6,673,568 | B1 * | 1/2004 | Fleming et al. | 435/34 |
| 6,676,655 | B2 * | 1/2004 | McDaniel | 606/9 |
| 6,787,302 | B2 * | 9/2004 | Fleming et al. | 435/4 |
| 7,112,806 | B2 * | 9/2006 | Lussier | 250/458.1 |
| 7,774,979 | B2 * | 8/2010 | Hurst | 47/58.1 LS |
| 7,905,052 | B2 * | 3/2011 | Hurst et al. | 47/29.4 |
| 8,145,295 | B2 * | 3/2012 | Boyden et al. | 600/476 |
| 8,180,436 | B2 * | 5/2012 | Boyden et al. | 600/476 |
| 8,187,824 | B2 * | 5/2012 | Lindsey | 435/7.23 |
| 8,546,088 | B2 * | 10/2013 | Lindsey | 435/7.2 |
| 2003/0004556 | A1 * | 1/2003 | McDaniel | 607/88 |
| 2004/0033555 | A1 * | 2/2004 | Anderson et al. | 435/34 |
| 2005/0072935 | A1 * | 4/2005 | Lussier | 250/458.1 |
| 2006/0016125 | A1 * | 1/2006 | Krauss et al. | 47/58.1 R |
| 2008/0120736 | A1 * | 5/2008 | Hurst | 800/276 |
| 2008/0298052 | A1 * | 12/2008 | Hurst et al. | 362/231 |
| 2009/0130700 | A1 * | 5/2009 | Ince et al. | 435/29 |
| 2010/0115830 | A1 * | 5/2010 | Dub | 47/17 |
| 2010/0159496 | A1 * | 6/2010 | Katsumata et al. | 435/29 |
| 2011/0172826 | A1 * | 7/2011 | Amodei et al. | 700/266 |

OTHER PUBLICATIONS

Norman, D.C.C.; Webb, D.J. and Pechstedt, R.D., "Interferometric Sensor Interrogation Using an Arrayed Waveguide Grating", Jan. 2005, IEEE Photonics Technology Letters, vol. 17, No. 1.*

Senger, H. and Hermsmeier, D., "UV—A/Blue-Light Responses in Algae", 1994, International Lighting in Controlled Environments Workshop, NASA-CP-95-3309.*

Marrow, R.C., "Submersible LED Lighting for Photobioreactors (SLLP)", May 2006, Orbital Technologies Corporation, Retrieved from the Internet on Feb. 26, 2013 at "http://www.reeis.usda.gov".*

* cited by examiner

740nm

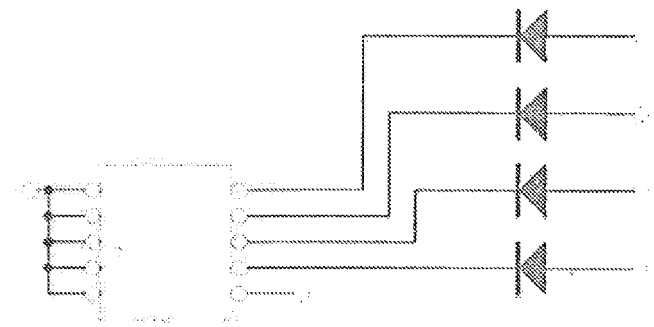
FIGURE 19
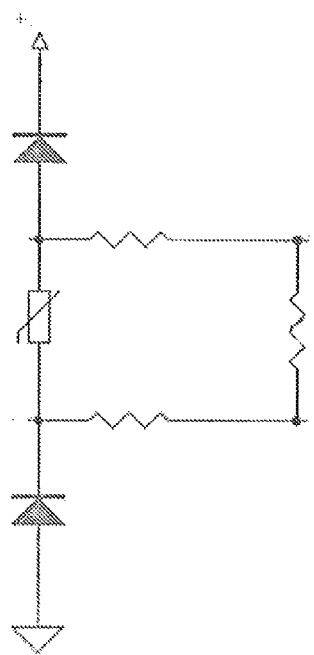

APPARATUS AND METHOD FOR PLANT METABOLISM MANIPULATION USING SPECTRAL OUTPUT

CROSS REFERENCE TO RELATED APPLICATIONS

This patent application is entitled to the benefit of Provisional Patent Application No. 61/083,886 filed on Jul. 25, 2008 in the USPTO.

FIELD OF THE INVENTION

This invention relates to illumination and radiant energy, and more specifically, to an apparatus and method for plant metabolism manipulation using spectral output.

BACKGROUND OF THE INVENTION

It has long been well known that proper lighting is a key ingredient in promoting robust and healthy plant growth. It is also known that optimized spectral outputs can be achieved to meet the specific needs of various plants during their growth phases. Known grow lamps are very energy intensive and adapted for delivering a high lumen output. Wattages of these high intensity arc-tube lamps range from 400 W to 1100 W. In commercial hydroponic and horticultural applications many of these lamps may be required. Therefore, it is readily observed that the aggregate power consumption of these types of lamps in a commercial operation is large and hence expensive. Much of the electrical energy consumed by a high intensity lamp is wasted in the form of heat. With rising energy costs there is a need to reduce the power consumption of grow lamps while maintaining their ability to stimulate desired plant growth. It is further desired to have a low energy consumption device that produces photosynthetically active radiation (PAR) at wavelengths that are usable by the plants. It is also further desired to have a grow lamp able to withstand the humidity and aerosol water droplets commonly found in greenhouse environments. It is further desired to have a lamp which needs little or no maintenance. It is further desired to have a lamp with an exceedingly long depreciation curve and working life.

Other sources of light, for example light emitting diodes (LEDs), are known to be capable of producing useful PAR with relatively small power consumption, virtually no heat, and a very long life. Therefore, these other sources of light, for example LEDs, can be adapted as grow lamps to offer a solution to the high power consumption of high intensity lamps.

Another shortcoming of current high intensity grow lamps is that they produce light by electrically arcing open current between an anode and cathode for the purpose of heating of high pressure gasses to a state of excited black body emission. This is essentially the same primitive principle resulting in the glow from an electric range element, except in that case the electricity stays safely within the heating element. The problem is that much of the power released in an arc lamp is emitted as photons which are directionally indiscriminately. Furthermore, the energy released falls largely in bands of the spectrum that are not useful for the stimulation of plant growth, indeed, there is evidence that the light power emitted by such systems may be detrimental to stages of plant development not directly involved in perennial harvest.

In our research, we have found that photosynthesis is not the sole use of light made by plants. Although they do get their primary operational energy source from photosynthesis, it has become clearer that many parts of the spectrum are used for environmental signalling in several dimensions. For example, competition for sunlight from other biota, temporal signals of both sidereal and seasonal cycles, atmospheric temperatures, the presence or absence of cloud cover, are just a few of the photometric environmental signals being read and understood by plant (and other forms of) life.

It follows that LEDs will be useful in mimicking these environmental signals for existing natural plants of all descriptions, and may indeed be useful for sending specifically pre-programmed signals to genetically modified life forms including but not limited to plants.

Another useful example implementing this principle is the ability to continuously vary the power outputs of multiple bands of phototropic radiation. The greatest power is placed into those bands which feed photosynthesis. These are 450 nm-470 nm and 640 nm-670 nm. However, other notch spectral bands have been added for such environmental signals as day/night cycles (@730 nm), seasonal cycles (@600 nm), and competitive signals (@525 nm). There are other notch spectral bands of interest in the ultraviolet range which is the ultraviolet—An environmental signals lying between 360 nm-410 nm. These signals may trigger harsh condition preparedness in plant life.

One advantage of the present invention is that any or all of the wavelengths mounted in a particular manufacture of our light emitting computer (LEC) can be changed during automated assembly without pause to the construction process. When research discovers new spectral power bands of influence to any form of life, biochemical process, or inorganic process; an LEC can be manufactured to provide the power necessary at the time and level to influence or drive multiple (up to six in one embodiment of the invention) spectrally specific phototropic processes, which may be sequential or parallel in their progression through time.

The LEC of our invention is designed to provide an application program interface (API) to a user programming system or graphical user interface (GUI) for the on board embedded computer. This permits a plurality of programs to be written for execution on the LEC. These programs will provide continuously variable power control over a range of phototropic wavelength specific emitters to energize and otherwise influence specific responses from plant life.

It is intended that in one embodiment of our invention, the apparatus will be used for implementing Phototropic Morphosis Management System (PMMS) methodology by the larger agronomy community to explore all forms of phototropic signalling and photosynthesis manipulations for an infinite variety of plant growing configurations. Utilizing PMMS with the present invention will result in an increasing range of knowledge in the agronomy community, which is one of humanity's largest and oldest. The present invention is therefore well adapted to the establishment of an open source community within which new knowledge of phototropic influences and optimizations for plant and other forms of life will be implemented, shared, and traded in the form of PMMS programs created to be run on the various embodiments of our invention.

Thus is created an entire domain of intellectual property within the structure of the LEC to run PMMS software for users, who in turn may then create new individual and highly specific implementations of new examples of PMMS software for the purpose of influencing a particular plant to grow in a particular fashion, which new PMMS programs those users may then trade or share within the larger LEC using community.

SUMMARY OF THE INVENTION

Our invention comprises the following major components: a front end GUI, the previously mentioned PMMS and the LEC.

The GUI permits programming of the invention using all currently used operating systems. The GUI is also adaptable to hand held digital devices.

The PMMS ('Phototropic Morphosis Management System') is the application software used to drive the invention.

The LEC is the 'Light Emitting Computer' which emits the appropriate types, strengths, frequencies of photosynthetic light.

The apparatus is an intelligent device which can be networked in large serial and parallel arrays having a single master controller. Other devices can be designed to be placed into and interact with the network, such as environmental sensors and controls or security devices. In this way an LEC network and client side computer can be configured to automate and maintain large installations. Client control is achievable using a portable handheld device, remotely.

Two very adaptable applications of our invention include Aquaponics which are combined land-locked fish and hydroponics farms and High Rise Farming comprising urban conversions of existing skyscrapers and new architectures based on high density vertical farm implementations.

What follows are a few examples of possible configurations of our invention:

In one embodiment of our invention 150 watts of photosynthetically active radiation is emitted. This embodiment includes a twilight sidereal cycle phytochrome manipulator and photosynthesis promoting system.

In another embodiment of our invention 385 watts of photosynthetically active radiation is emitted. This embodiment includes networking means for a grid of up to 31×31 units.

In another embodiment of our invention there is a single 4 watt single plant illuminator having full spectral control and continuous power variability over four spectral power bands: 470 nm, 525 nm, 668 nm, and 730 nm utilizing and implementing the PPF-RGB-LED with on board physical controls and serial API implementation in arrays of up to 31×31 units.

In yet another embodiment of our invention there is a larger 12 watt single plant illuminator with full spectral control and continuous power variability over four spectral power bands: 470 nm, 525 nm, 668 nm, and 730 nm with on board physical controls and serial API implementation in arrays of up to 31×31 units.

In still another embodiment of our invention there is a 13 watt single plant illuminator with full spectral control and continuous power variability of four spectral power bands: 470 nm, 525 nm, 668 nm, and 730 nm utilizing and once again implementing the PPF-RGB-LED with on board physical controls and serial API implementation in arrays of up to 31×31 units.

In another embodiment of the invention there an emitter design of 585 watts which is fully programmable and has fully variable power output over six spectral power bands. This embodiment can be fully network.

In another embodiment of the invention, the emitters are selected to inhibit plant growth. Wavelengths that inhibit plant growth are between 600 nm and 610 nm. There are many applications where such an array of plant growth inhibiting LEDs can be applied such as street lights to inhibit plant growth around them while at the same time emitting visible yellow-orange light.

Modular embodiments of up to 10,000 watts for larger scale aeroponic applications are possible.

Therefore, the shortcomings and deficiencies of traditional technologies cited earlier are resolved by our invention which is an apparatus for plant metabolism manipulation using spectral output comprising an array of light sources having photosynthetic promoting spectral emissions, means for controlling the spectral emissions in a programmable manner operatively connected to the array and a power source operatively connected to the array and the means for controlling the spectral emissions.

To promote plant growth the array does not contain any sources of spectral emissions that have known deleterious effects on plant growth such as UV-b and UV-c. The array has no known electromagnetic emission of any description beyond those intended by design. However, in other embodiments of the invention the array may have light sources that do contain spectral emissions that inhibit plant growth for applications such as control of unwanted plant growth such as weed control applications. A good example of this application would be to have a lighting array installed on a highway having spectral emissions that would deter plant growth on road shoulders while at the same time providing a suitable level of light for traffic.

In other embodiments of the invention the lighting array has spectral emissions that are adapted to specific industrial uses such as curing paint, ink or adhesives. Other embodiments may have spectral emissions that aid in non-destructive testing of manufactured parts.

In one embodiment of the invention the array of light sources comprises a first plurality of identical light sources having a first spectral emission, a second plurality of identical light sources having a second spectral emission and a third plurality of identical light sources having a third spectral emission.

In other embodiments of the invention, there may be additional pluralities of light sources having other spectral emission characteristics to suit the application some of which are exemplified above. The photosynthetic characteristics of any plant can be used to design a grow lamp having an array of light sources with photosynthetic promoting characteristics and lacking growth inhibiting spectral emissions.

In one embodiment of the invention the first, second and third pluralities of light sources populate a respective first, second and third distinct surface areas of the array.

In another embodiment of the invention the first, second and third pluralities of light sources are mixed to populate the entire surface of the array. Again, the arrangement of light sources on the array is determined by the photosynthetic characteristics of the plant of interest for optimized stimulation or repression of photosynthesis and other phototropic metabolic functions as desired.

In one embodiment of the invention the light source array is fixed to a circuit board. In another embodiment of the invention the first, second and third spectral emissions are at respective first, second and third photosynthetic promoting wavelengths. In other embodiments of the invention there may be a combination of light sources that promote growth of certain plants but inhibit growth of other plants.

The control means comprises a programmable microcontroller (with internal battery-backed-up clock) adapted to transmit commands to the array of light sources. The commands include, for each specific light source plurality, on and off commands at up to 36 Khz, providing functional intensity control as well as 'on' and 'off' control signals. The array can be programmed to suit any lighting condition desired for optimizing photosynthesis and other phototropic metabolic functions in a plant of interest.

The commands may also include pre-glow and afterglow commands to simulate dawn and sunset. In other embodiments the commands may include commands that inhibit growth of undesirable plants at specific and vulnerable states of their growth cycle. In operation, the programmable controller is adapted to command the array of light sources to emit predetermined wavelengths of energy falling within a range of photosynthetic promoting energy for a predetermined period of time.

The power source is an AC power source in one embodiment of the invention and a DC power source in another embodiment of the invention.

The invention also includes a method for plant metabolism manipulation using spectral output comprising the steps of:
 a. Determining the photosynthetic properties of a plant of interest;
 b. Fabricating an array of light sources comprising in combination desired pluralities of light sources having 6 desired spectral emissions of various maximum power potentials that are compatible with the photosynthetic and other phototropic properties of the plant of interest;
 c. Placing the plant of interest in desirable proximity to the array of light sources; and,
 d. Operatively connecting a programmable microprocessor to the array of light sources wherein the programmable microprocessor is adapted to transmit commands to the desired pluralities of light sources so that they emit the desired spectral emissions at a desired time and for a desired period at a desired intensity.

The method may also include the step of simulating a predawn glow. The method may also include the step of simulating an after sunset glow. In another embodiment of the invention the method may also include the step of strobing specific pluralities of light sources for desired time intervals at desired intensities for various phototropic effects on plants or other light sensitive systems.

BRIEF DESCRIPTION OF THE DRAWINGS

FIG. 19 is a schematic of a communication option for the third embodiment.

DETAILED DESCRIPTION OF THE INVENTION

Figure 1:
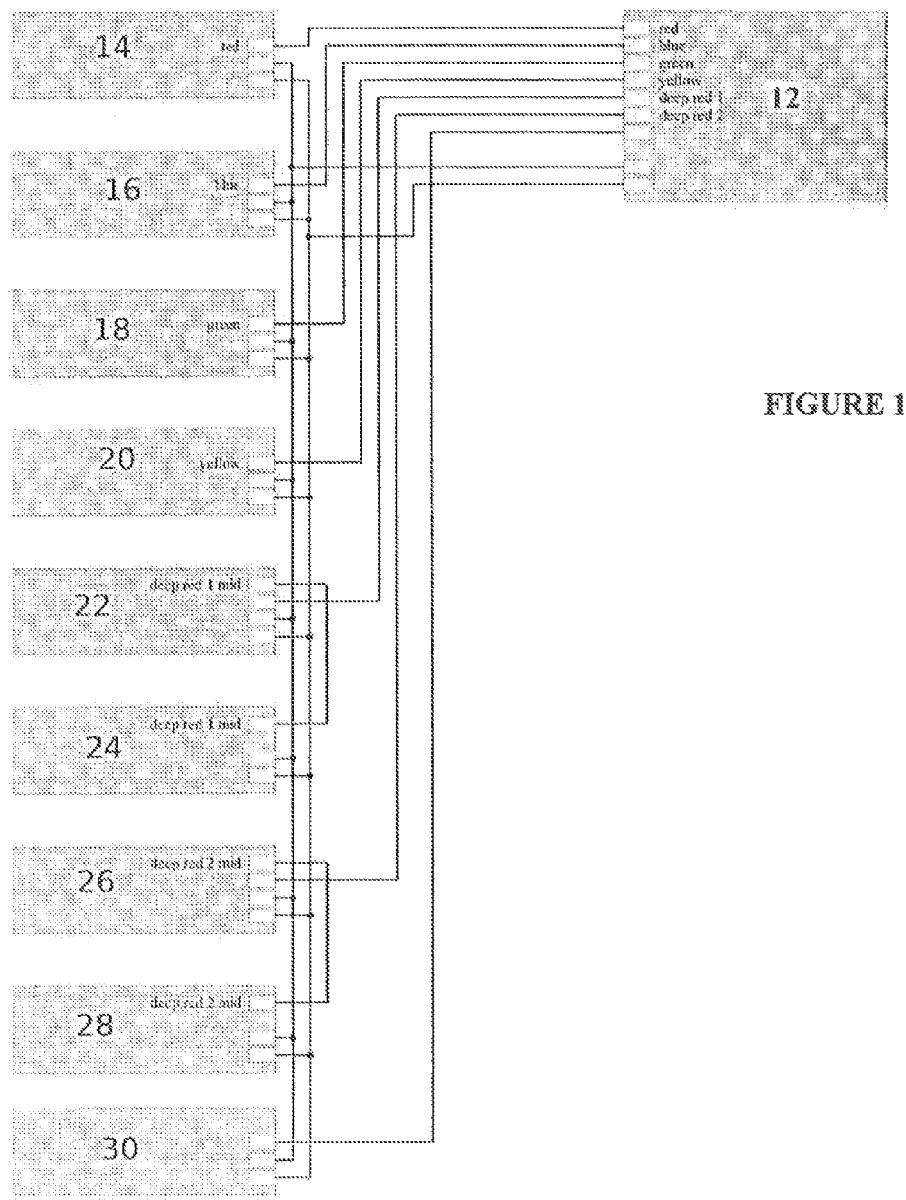
FIG. 1 is a schematic of a first embodiment of the invention.

The purpose of the invention is to advance the art of agriculture at the level of photo-sensitive biochemical activity in plants, particularly photomorphogenesis and photo-synthesis but not restricted to these positive applications. Specifically, the invention is adapted for programmable and controlled emission of phototropically active portions of the electromagnetic spectrum though both amplitude and time domain modulation which shall be then synchronized and harmonized with related metabolic processes to manipulate the target botanical.

The invention comprises an apparatus and method for plant metabolism manipulation using the spectral output of light sources such as LEDs. The use of a digitally controlled quantum mechanical source of light (such as an LED) rather than high intensity grow lamps offers to the inventor further advantages than merely the low power consumption, low heat output, and incredibly long useful life spans found elsewhere in the LED lighting industry; but further improves the state of the art through the utilization of special properties of LED such as selective spectral wavelength output and most especially through the ability to infinitesimally manipulate the various time domains of plant exposure to specific levels of energy at those specific spectral wavelengths.

The light source emitters can be configured in any combination of desired wavelengths to suit specific plant photosynthesis and other phototropic metabolic functions needs during propagation, vegetation and the fruiting/flowering stage. Alternatively the light source emitters can be configured to inhibit plant growth of unwanted plants as well as other industrial applications such as curing paint or adhesives. As well, the emitters can be oriented in any direction and in close proximity to the plants without burning them with waste heat. The emitter of this invention is computer controlled. As such, it represents a significant step forward in the state of the art of grow lamps. Prior art grow lamps are not capable of accurately simulating the type of light a plant would receive at dawn (pre-glow) or at dusk (after-glow) as the sun rises and sets. The ability to simulate this type of light in a grow lamp has a positive effect on plant growth and improves the ability to manipulate plant metabolism. Other advantages of computer controlled spectral emissions of our invention include the ability to force flowering, manipulate inter-nodal distances, initiate vegetative regression, and drive root propagation.

In one embodiment of the invention which is exemplary only there is a light source comprising an array of LEDs comprising 100 735 nm 120 mW 5 mm thru-hole LEDs, 900 660 100 mW 5 mm thru-hole LEDs, 1 MCPCB-star mounted 1 W 660 nm LED, 35 MCPCB-star mounted 1 W 640 nm LEDs, 4 MCPCB-star mounted 1 W 610 nm LEDs, 4 MCPCBstar mounted 3 W 530 nm LEDs and 6 MCPCB-star mounted 3 W 450 nm LEDs. These are computer controlled and mounted to a circuit board.

In another embodiment of the invention there is a circuit board populated with a plurality of LEDs to form a grow lamp having 207×730 nm 180 mW SMD-PICC2 LEDs, 2880×660 nm 60 mW SMD-0603 LEDs, 3×610 nm 3 W SMD-Luxeon LEDs, 3×530 nm 3 W SMD Luxeon LEDs and 390×430 nm 150 mW SMD0805 LED. They are hunched in groups according to their spectral frequency and electrical characteristics. The LEDs are computer controlled and therefore we can turn off or on different groups, i.e. spectral frequencies (or ranges of frequencies). A microcontroller is placed on the lamp board which we use to turn on/off the different groups according to a schedule implemented in software which is user controlled by either jumpers on the board, or through a communications channel with some other device sending commands for the on hoard computer to follow.

In yet another embodiment of the invention there is the ability to vary the output power of each different frequency group by altering the current flowing through any sub-group. Currently, we are using a 24V 500+ W power supply that is off board and connected through a cable to the lamp array. We then have current limiting circuits for each subgroup emplaced upon the circuit board to control the current through the various groups of light sources. The micro-controller turns on and off different groups at different times by way of a switch controlling power to said modules. Relays are used for switches. In another embodiment of the invention there is variable output current control having a switching function built in.

The light source array can be programmed to a wide variety of uses in the fields of botanical research and agricultural production techniques.

The light source array can comprise a wide variety of wavelength and intensity 'blends'. For example, one array May comprise:

5 W of 730 nm
30 W of 660 nm
10 W of 645 nm
10 W of 530 nm
20 W of 470 nm

The light source array can be programmed to strobe at a variety of frequencies, intensities and periods.

In another example of the invention the following proportions of LEDs might be used:

19%; 430 nm
17% 450 nm
2% 530 nm
2% 610 nm
50% 660 nm
10% 730 nm

This array of LEDs is supplied by a constant power and programmable for various light on/off cycles such as 6/18, 12/12 and 18/6. There is also an afterglow of 730 nm for about one hour right after the lights are turned off fir each cycle.

Another embodiment of the invention uses an array of light sources comprising emissions in the range of 360 nm to 410 nm, 450 nm to 470 nm, 520 to 530 nm, 590 nm to 615 nm, 640 nm to 670 nm, and 720 nm to 890 nm with each wavelength operated using a dedicated controller. A micro-processor is then used to adjust the quality of the light emitted as the exposed plant matures. Since the light sources are placed on a large sized array, for example 40 cm by 40 cm, it is necessary to ensure, that the exposed plant receives the appropriate amount of energy at the proper wavelength. To this end, the light sources may be equipped with holographic thin film Fresnel lenses that refract light to the plant. The closer the emitters are to the plant the greater the angle will have to be. In one embodiment of the invention emitters with holographic thin film Fresnel lenses creating a radiating arc in the range of 140 degrees are used.

A FIRST EXAMPLE OF THE INVENTION

Referring now to FIGS. 1 to 10 inclusive there is illustrated a first example of the invention. In FIG. 1, there is shown a top-level schematic for one embodiment of the invention. The invention comprises a controller 10 electrically connected to a plurality of LED arrays comprising red 14, blue 16, green 18, yellow 20, deep red 1 22, deep red 2 24, deep red 3 26 and deep red 4 28. The circuit permits the addition of an optional array 30. The LED arrays can be made to strobe up to a frequency of 39 KHz.

Figure 2:
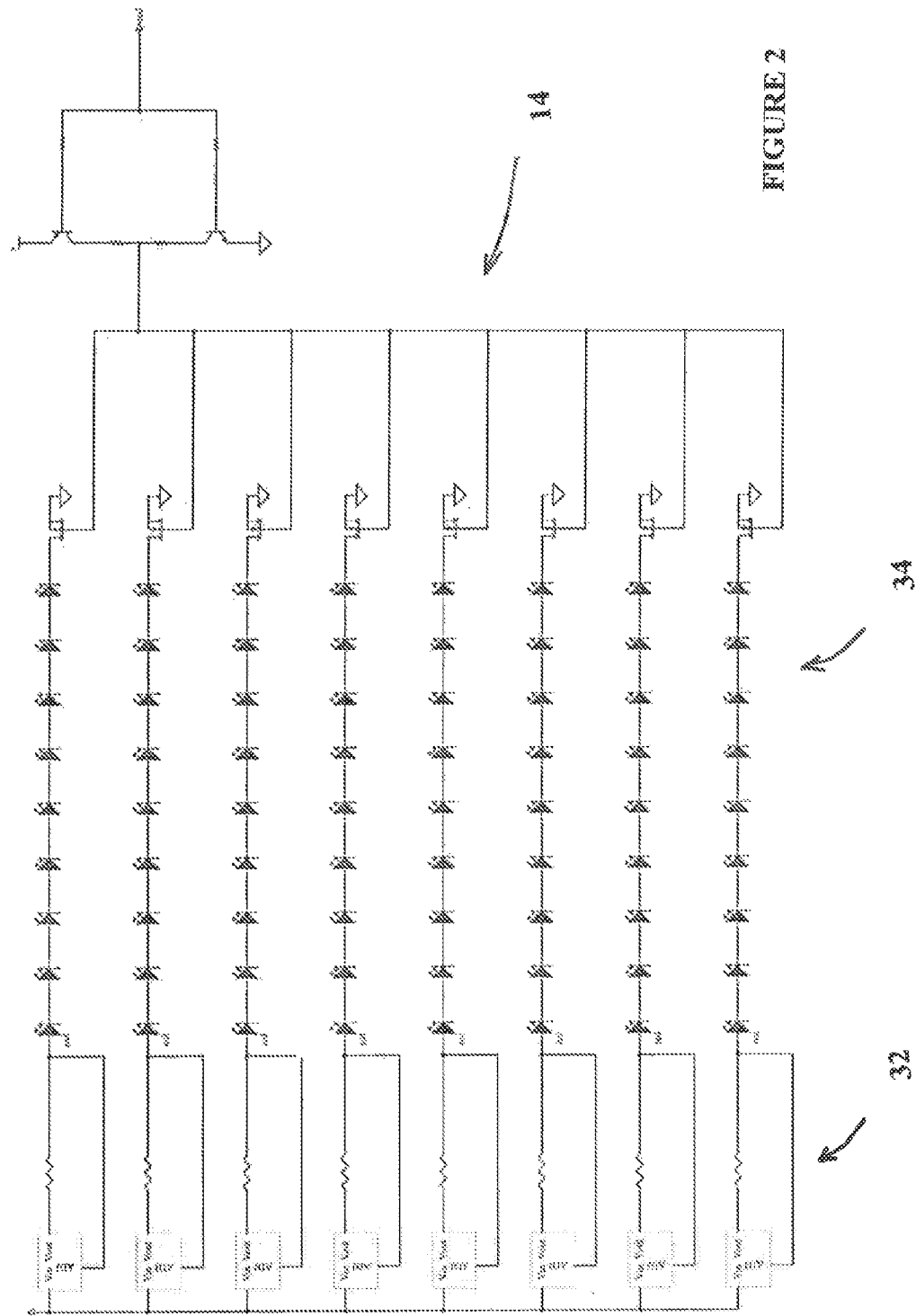
FIG. 2 is a schematic of the red LED array of the first embodiment.

FIG. 2 shows red circuit 14 comprising power connections 32 and a 9 by 8 array of LEDs 34.

Figure 3:
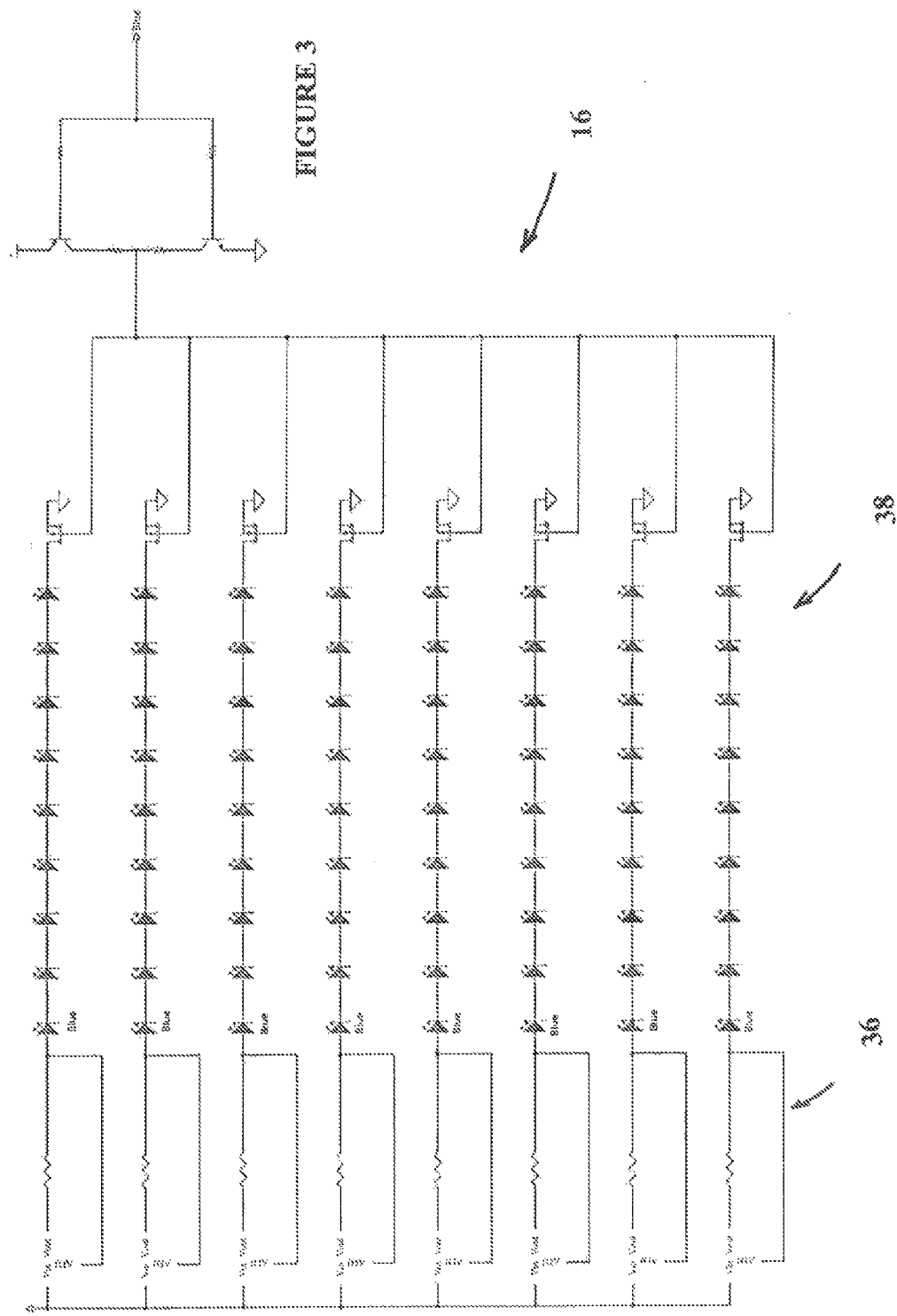
FIG. 3 is a schematic of the blue LED array of the first embodiment.

FIG. 3 shows blue circuit 16 comprising power connections 36 and a 6 by 12 array of LEDs 38.

Figure 4:
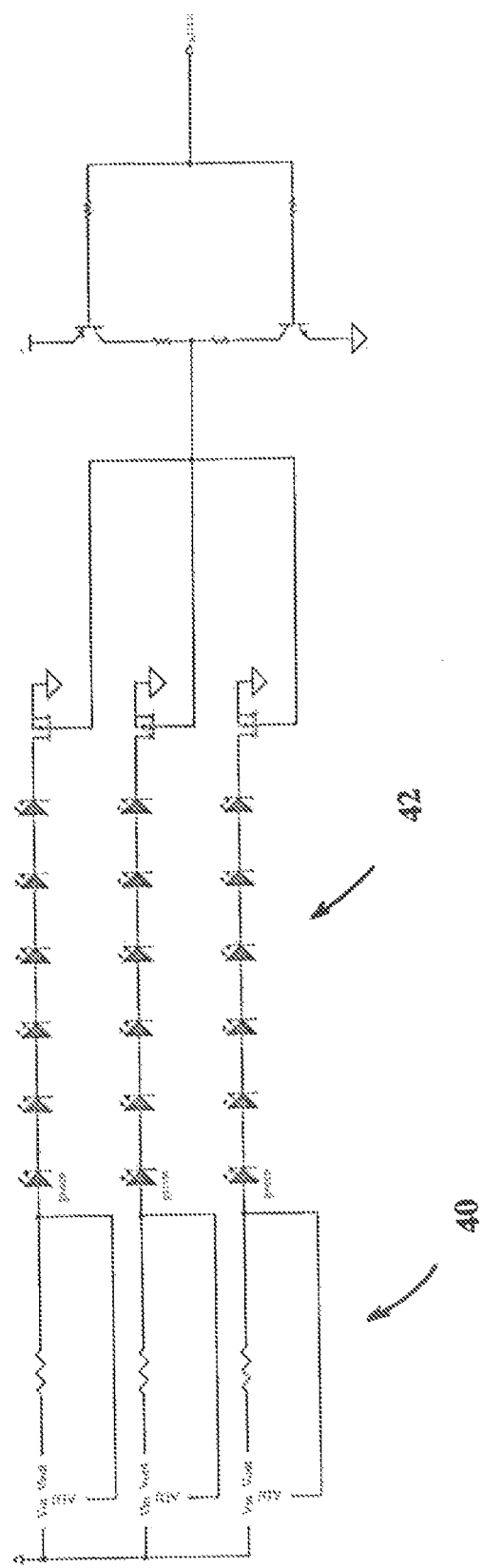
FIG. 4 is a schematic of the green LED array of the first embodiment.

FIG. 4 shows green circuit 18 comprising power connections 40 and a 6 BY 3 array of LEDs 42.

Figure 5:
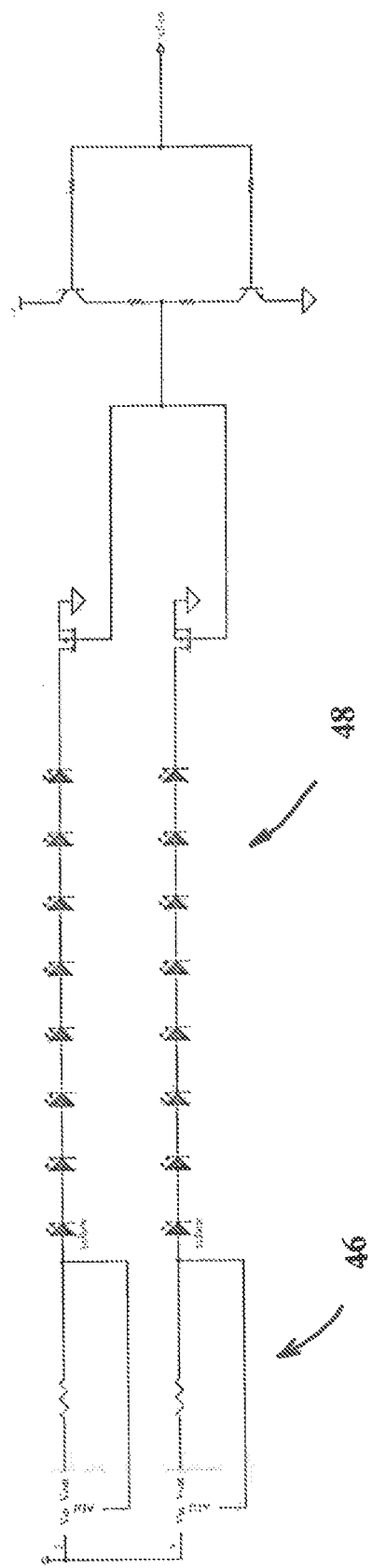
FIG. 5 is a schematic of the yellow LED array of the first embodiment.

FIG. 5 shows yellow circuit 20 comprising power connections 46 and a 2 by 8 array of LEDs 48.

Figure 6:
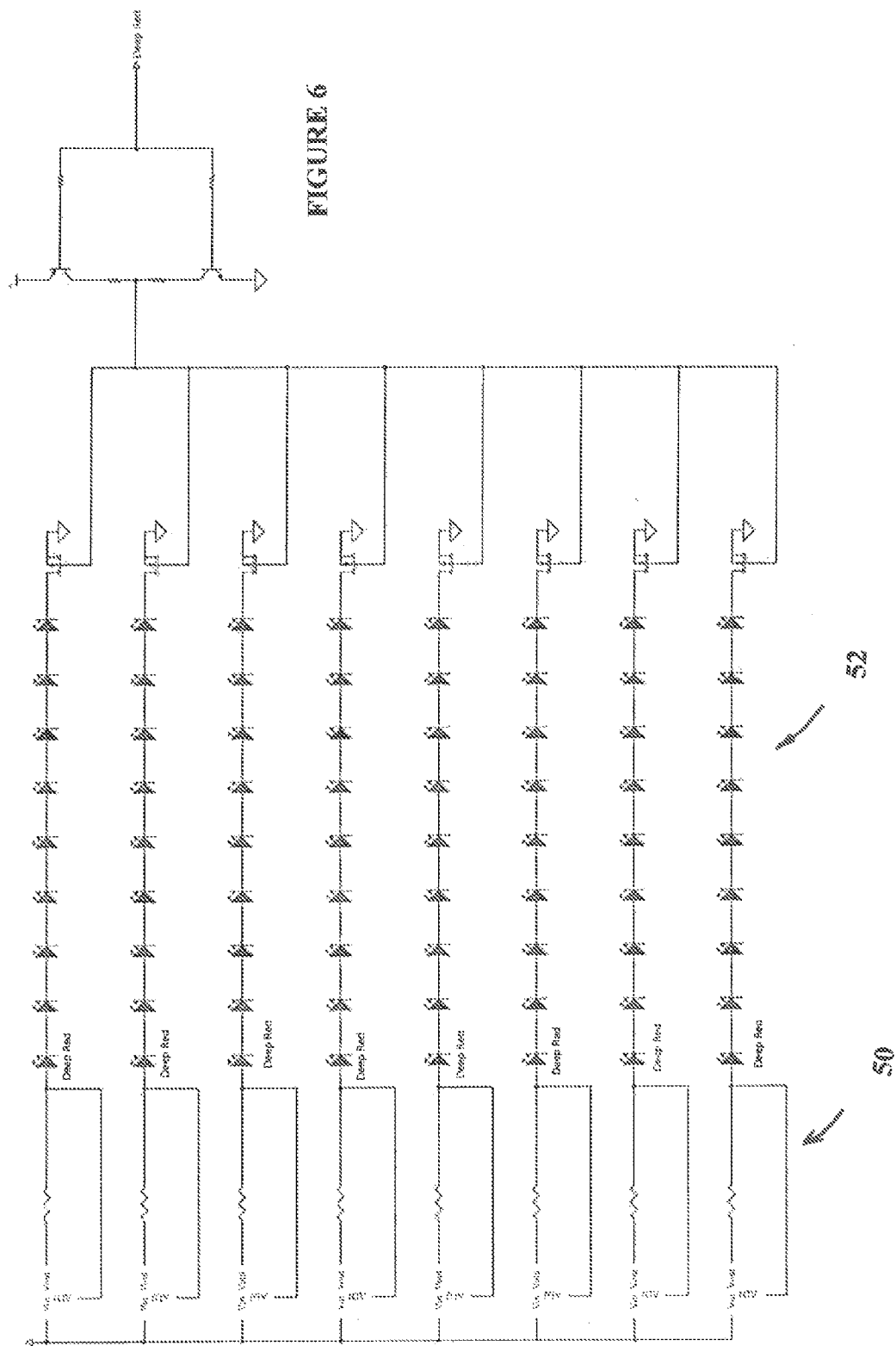
FIG. 6 is a schematic of the deep red #1 LED array of the first embodiment.

FIG. 6 shows deep red circuit #1 22 comprising power connections 50 and An 11 by 6 array of LEDs 52.

Figure 7:
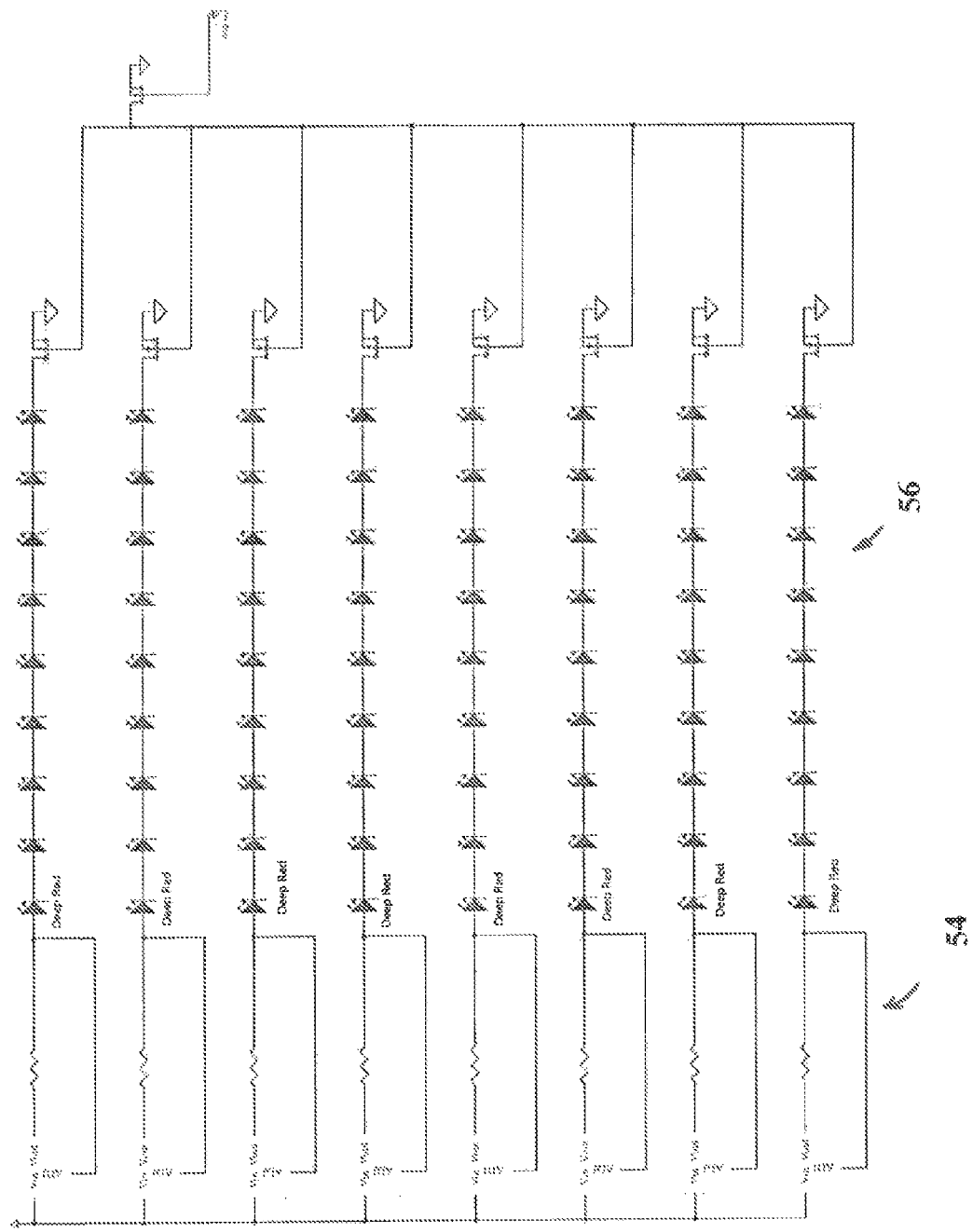
FIG. 7 is a schematic of the deep red #2 LED array of the first embodiment.

FIG. 7 shows deep red circuit #2 24 comprising power connections 54 and an 11 by 6 array of LEDs 56.

Figure 8:
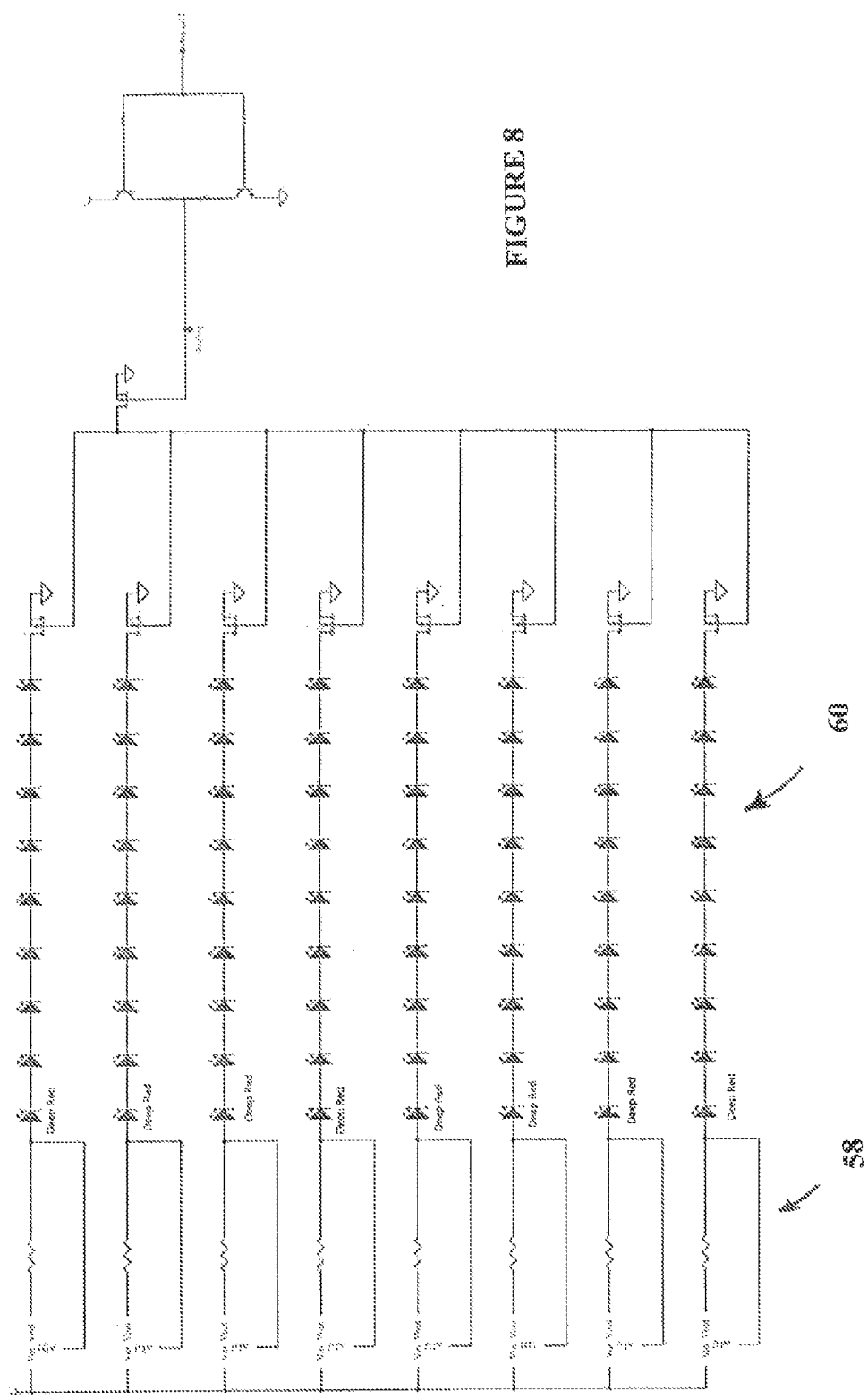
FIG. 8 is a schematic of the deep red #3 array of the first embodiment.

FIG. 8 shows deep red circuit #3 26 comprising power connections 58 and an 11 by 6 array of LEDs 60.

Figure 9:
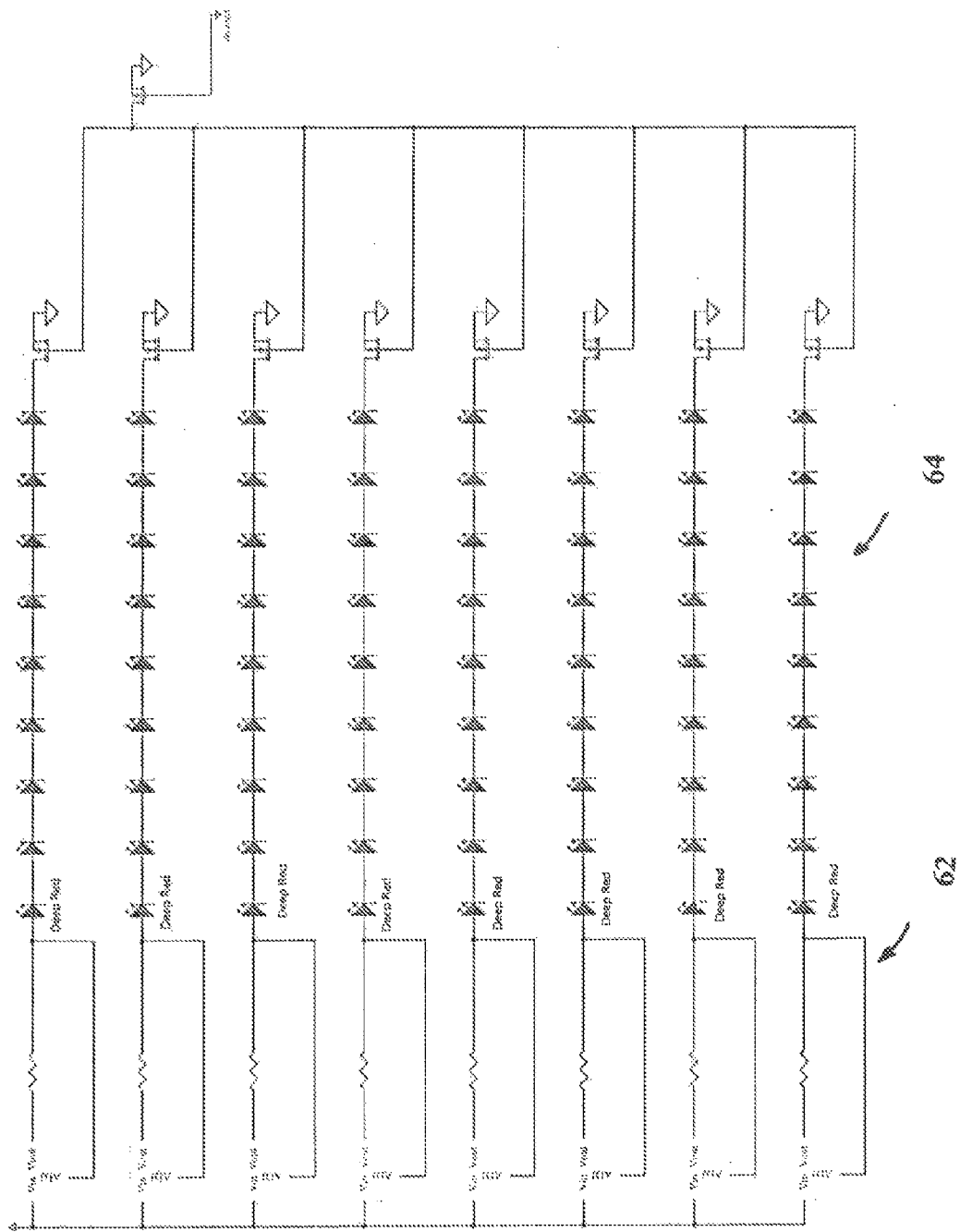
FIG. 9 is a schematic of the deep red #4 array of the first embodiment.

FIG. 9 shows deep red circuit #4 28 comprising power connections 62 and an 11 by 6 array of LEDs 64.

Figure 10:
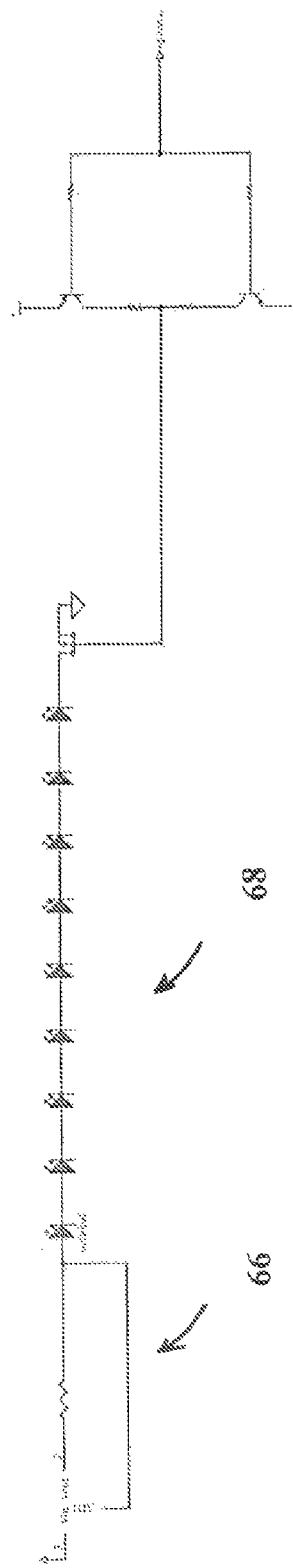
FIG. 10 is a schematic of the optional array of the first embodiment.
Figure 11:
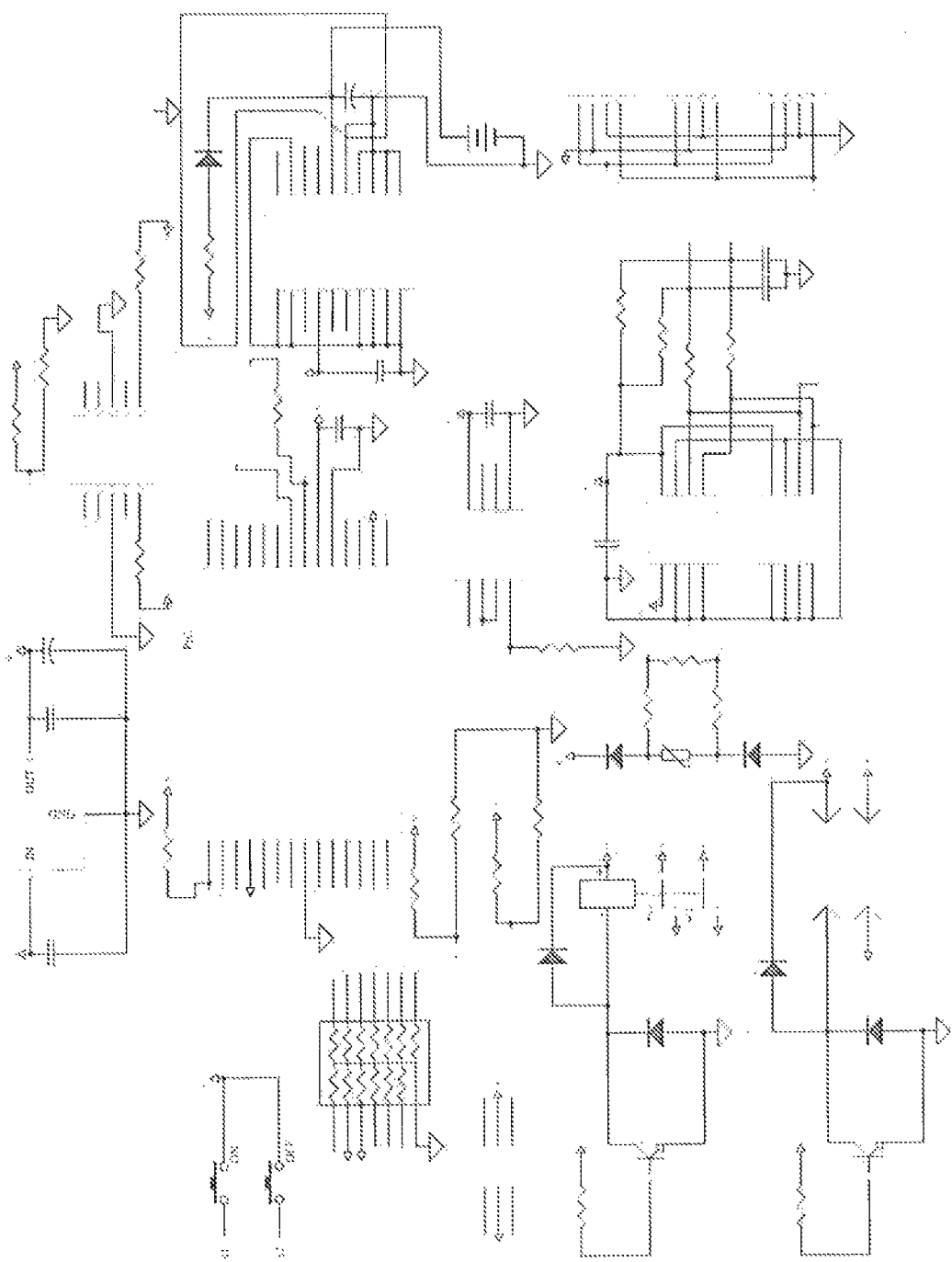
FIG. 11 is a schematic of a second embodiment of the invention.

FIG. 10 shows optional circuit 30 comprising a power connection 66 and a 1 by 9 array of LEDs 68.

A SECOND EXAMPLE OF THE INVENTION

Referring now to FIG. 11 to 18 there is shown a second example of the invention.

FIG. 1 shows a control schematic of one embodiment of the invention.

Figure 12:
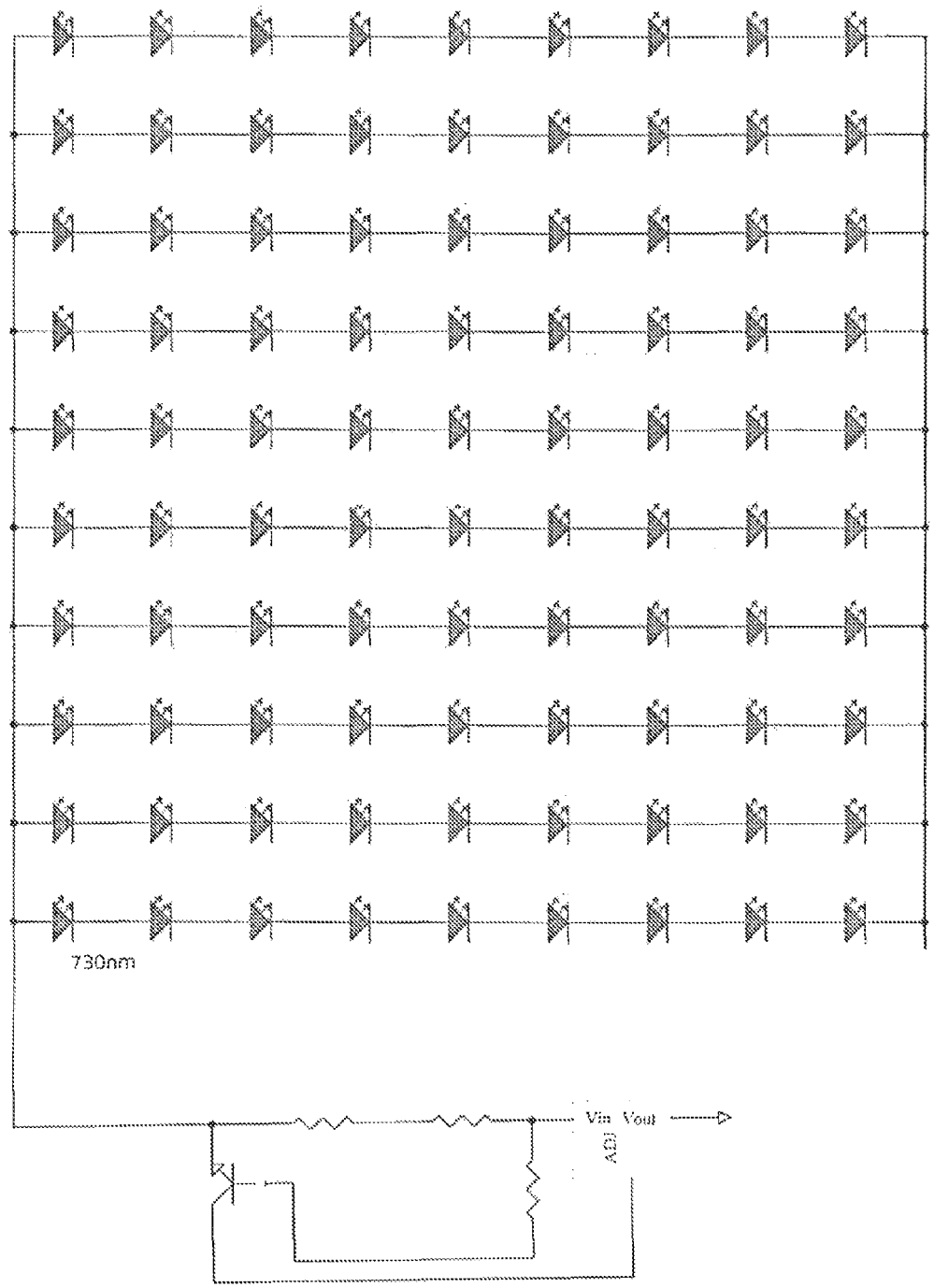
FIG. 12 is a schematic of the 730 nm array of the second embodiment.

FIG. 12 shows a circuit comprising a grid array of 9 by 10 LEDs having a wavelength of 730 nm.

Figure 13:
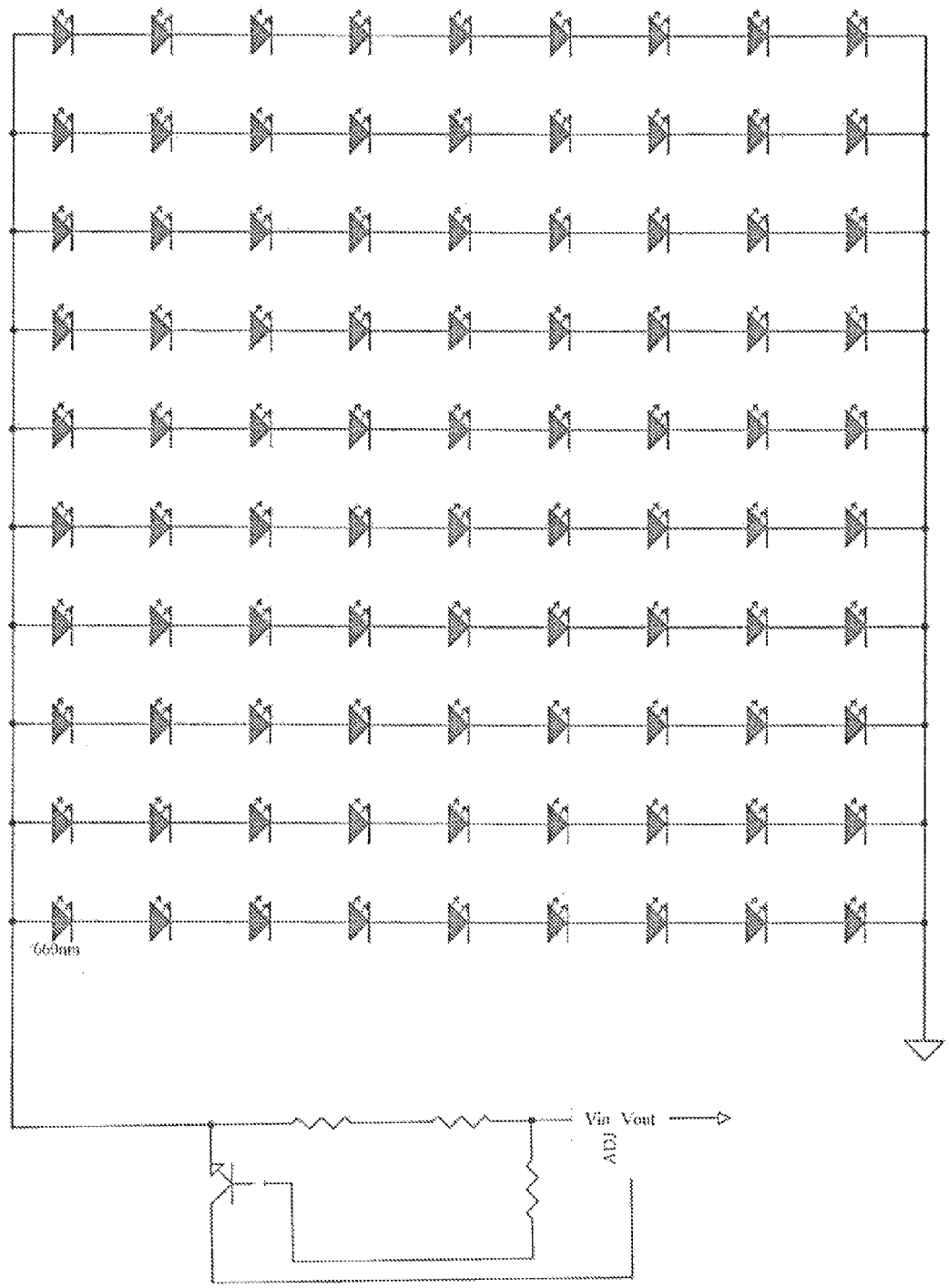
FIG. 13 is a schematic of the 660 nm array of the second embodiment.

FIG. 13 shows a circuit comprising a grid array of 9 BY 10 LEDs having a wavelength of 660 nm.

Figure 14:
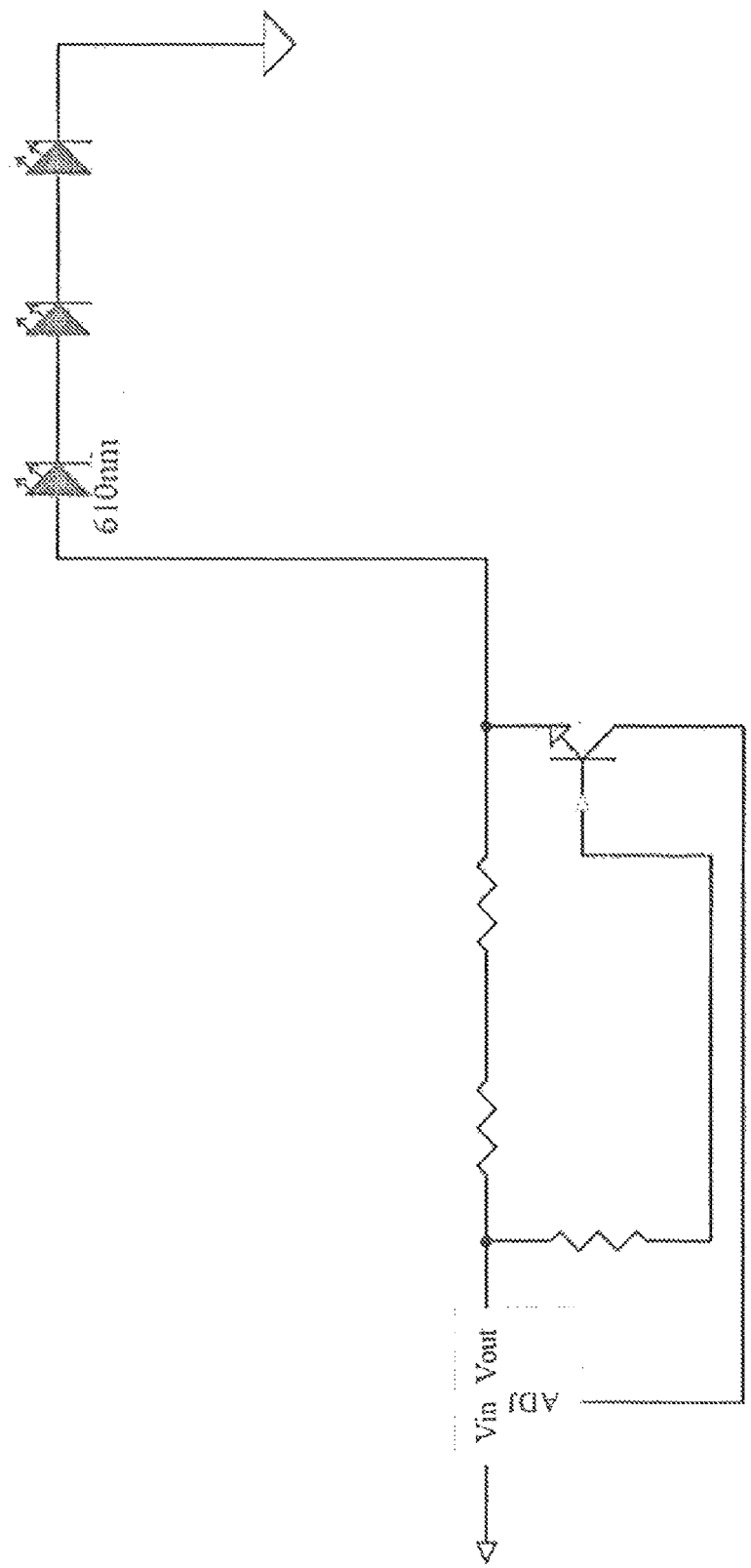
FIG. 14 is a schematic of the 610 nm array of the second embodiment.

FIG. 14 shows a circuit comprising a grid array of 1 by 3 LEDs having a wavelength of 610 nm.

Figure 15:
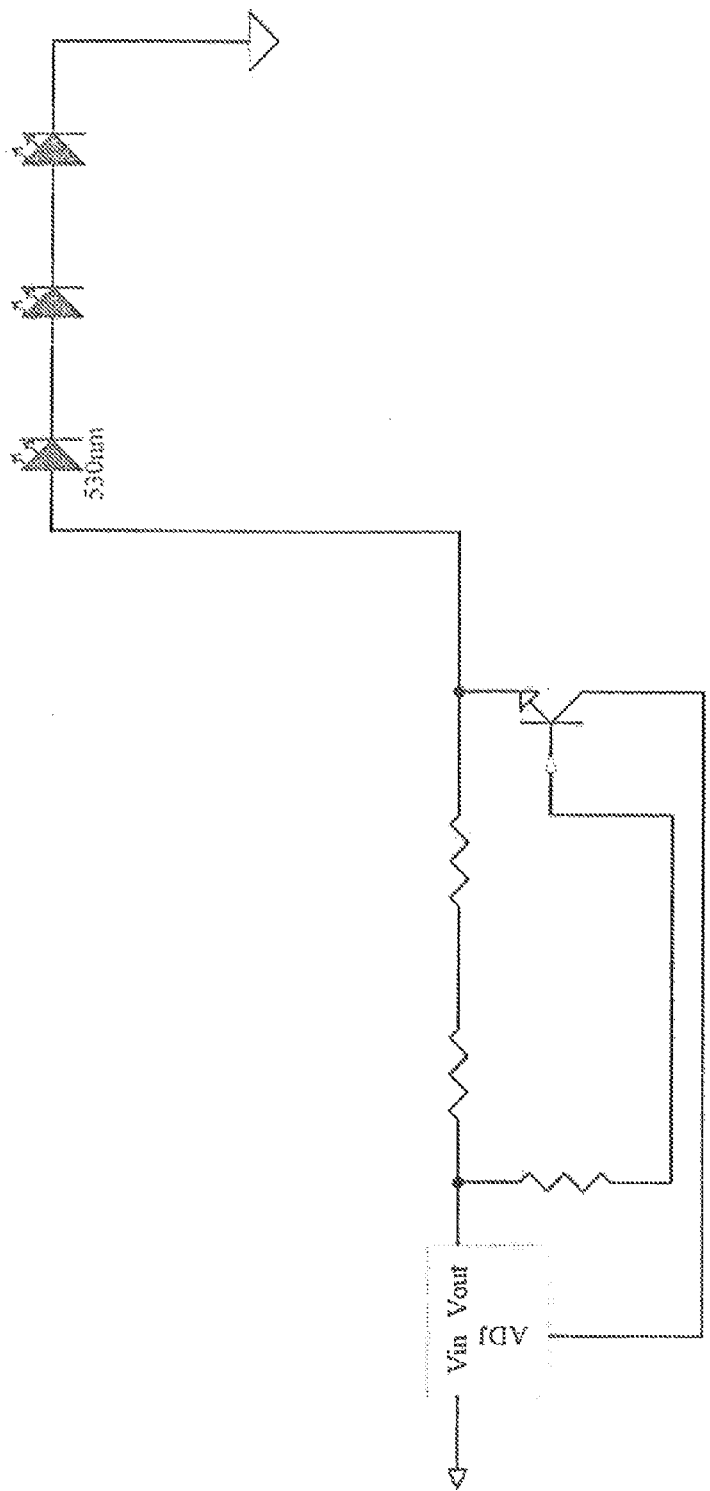
FIG. 15 is a schematic of the 530 nm array of the second embodiment.

FIG. 15 shows a circuit comprising a grid array of 1 by 3 LEDs having a wavelength of 530 nm.

Figure 16:
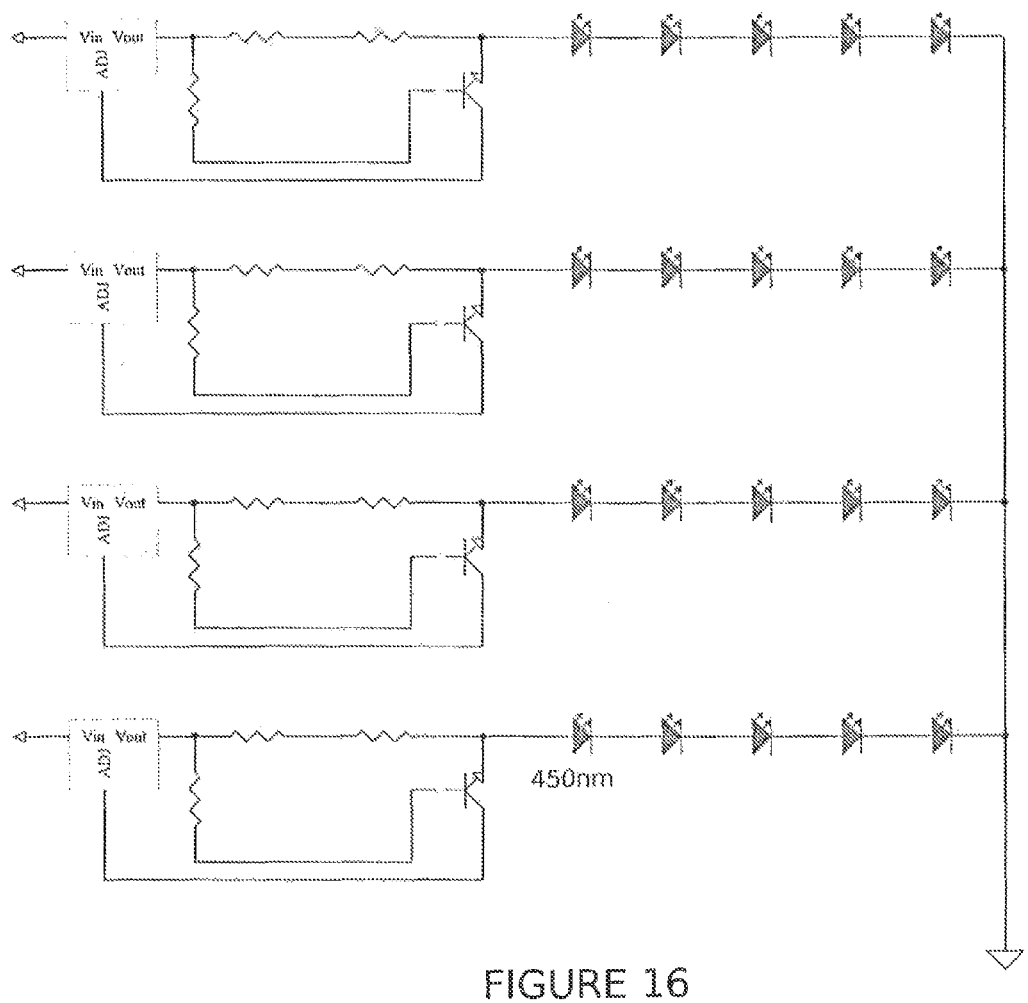
FIG. 16 is a schematic of the 450 nm array of the second embodiment.

FIG. 16 shows a circuit comprising a grid array of 5 by 4 LEDs having a wavelength of 450 nm.

Figure 17:
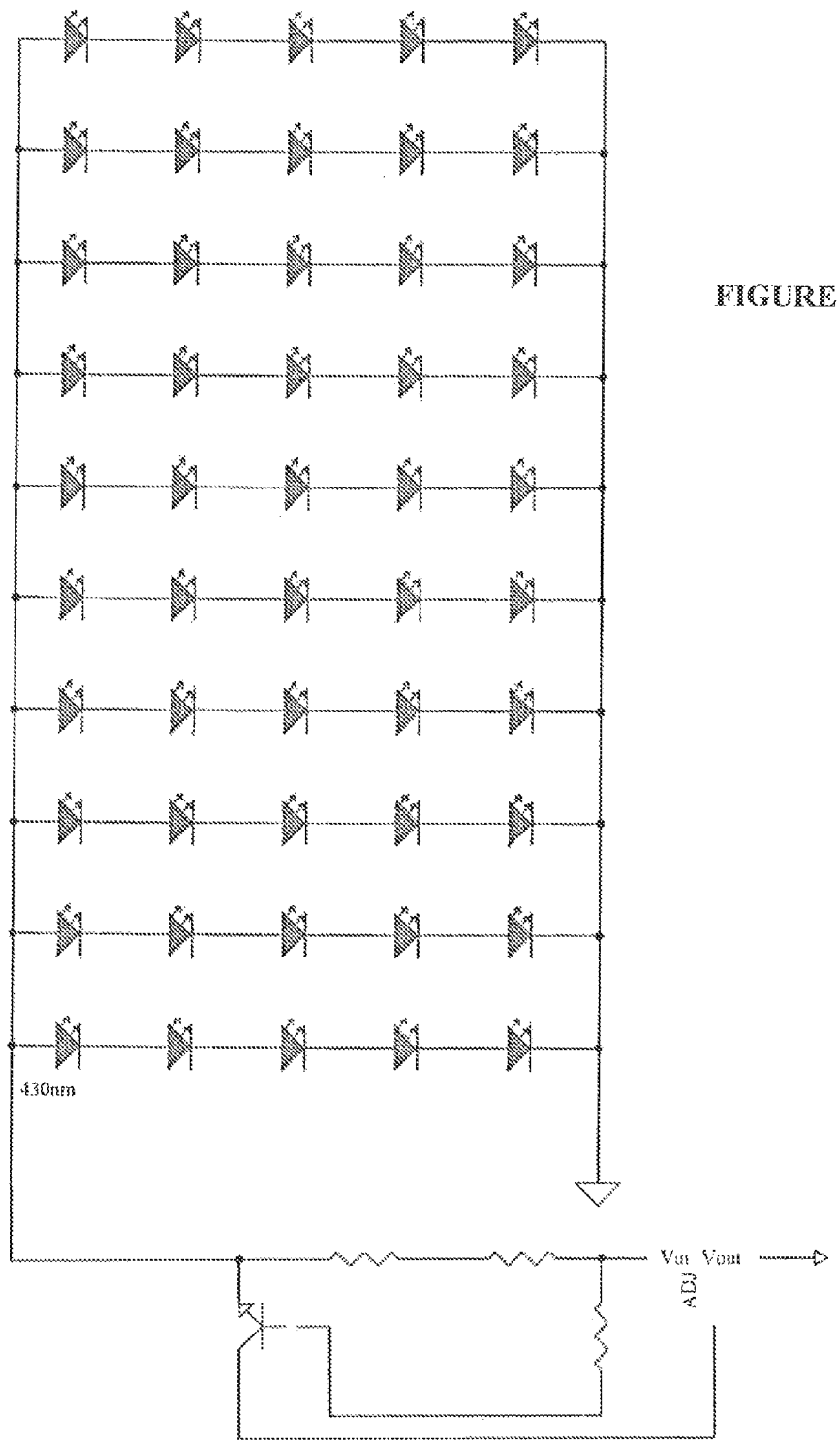
FIG. 17 is a schematic of the 430 nm array of the second embodiment.

FIG. 17 shows a circuit comprising a grid array of 5 by 10 LEDs having a wavelength of 430 nm.

A THIRD EXAMPLE OF THE INVENTION

Figure 18:
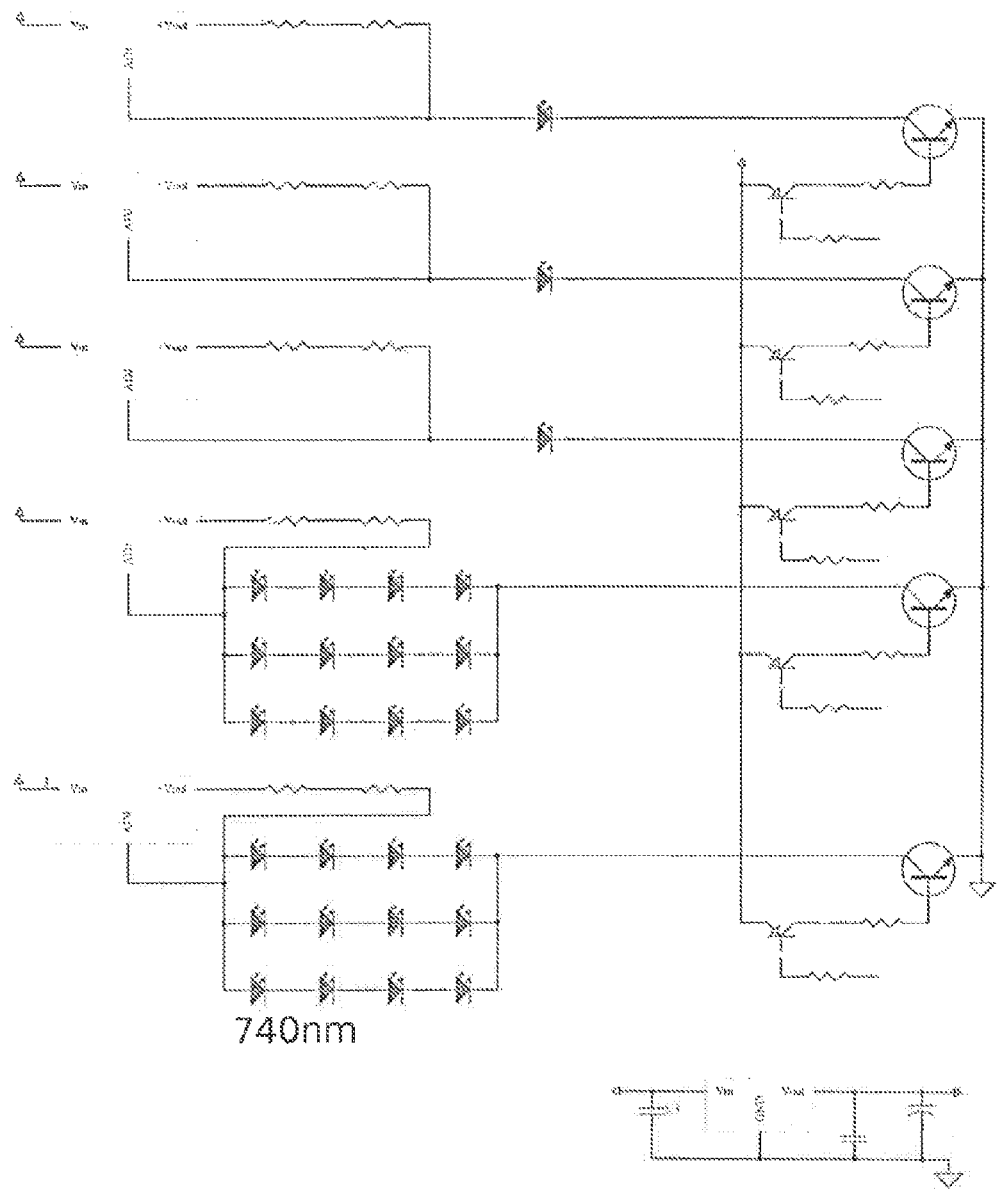
FIG. 18 is a schematic of a third embodiment of the invention.

Referring now to FIG. 18 there is shown a third example of the invention. This embodiment comprises a controller controlling two grid arrays of 4 by 3 LEDs at 740 nm.

FIG. 19 illustrates a communication option for this example, whereby the LED arrays can be controlled remotely.

Figure 20:
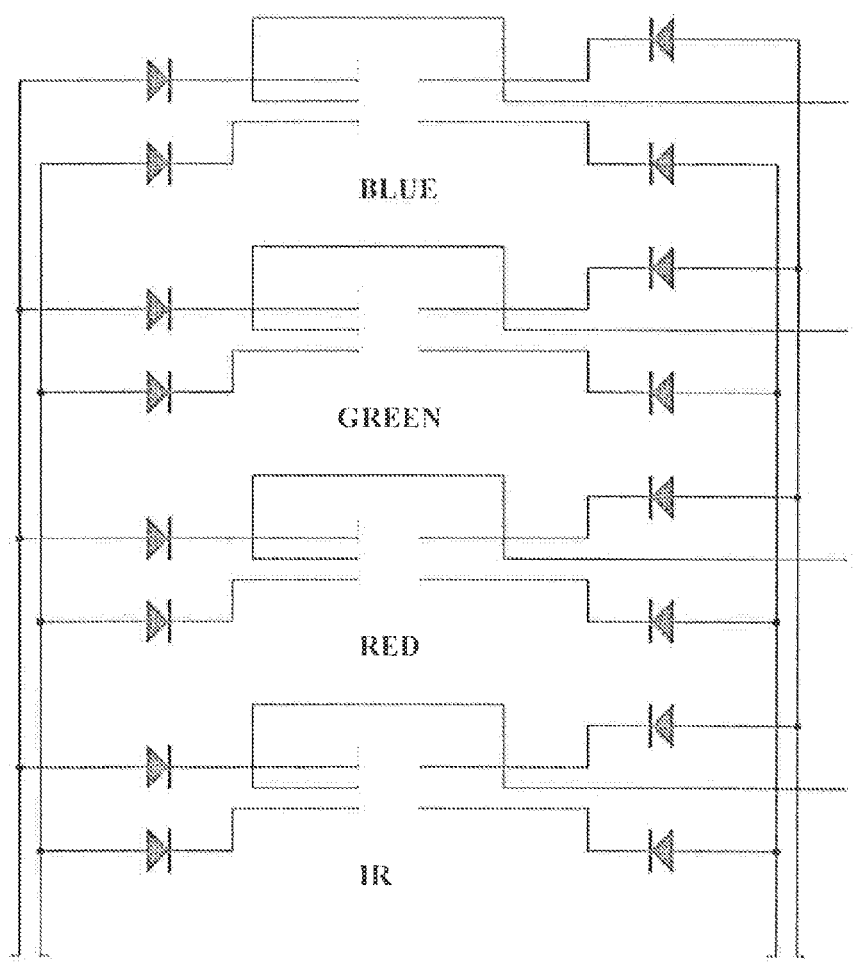
FIG. 20 is a schematic of the switch option for the third embodiment.

FIG. 20 illustrates an optional switching schema for this example of the invention.

A FOURTH EXAMPLE OF THE INVENTION

Figure 21:
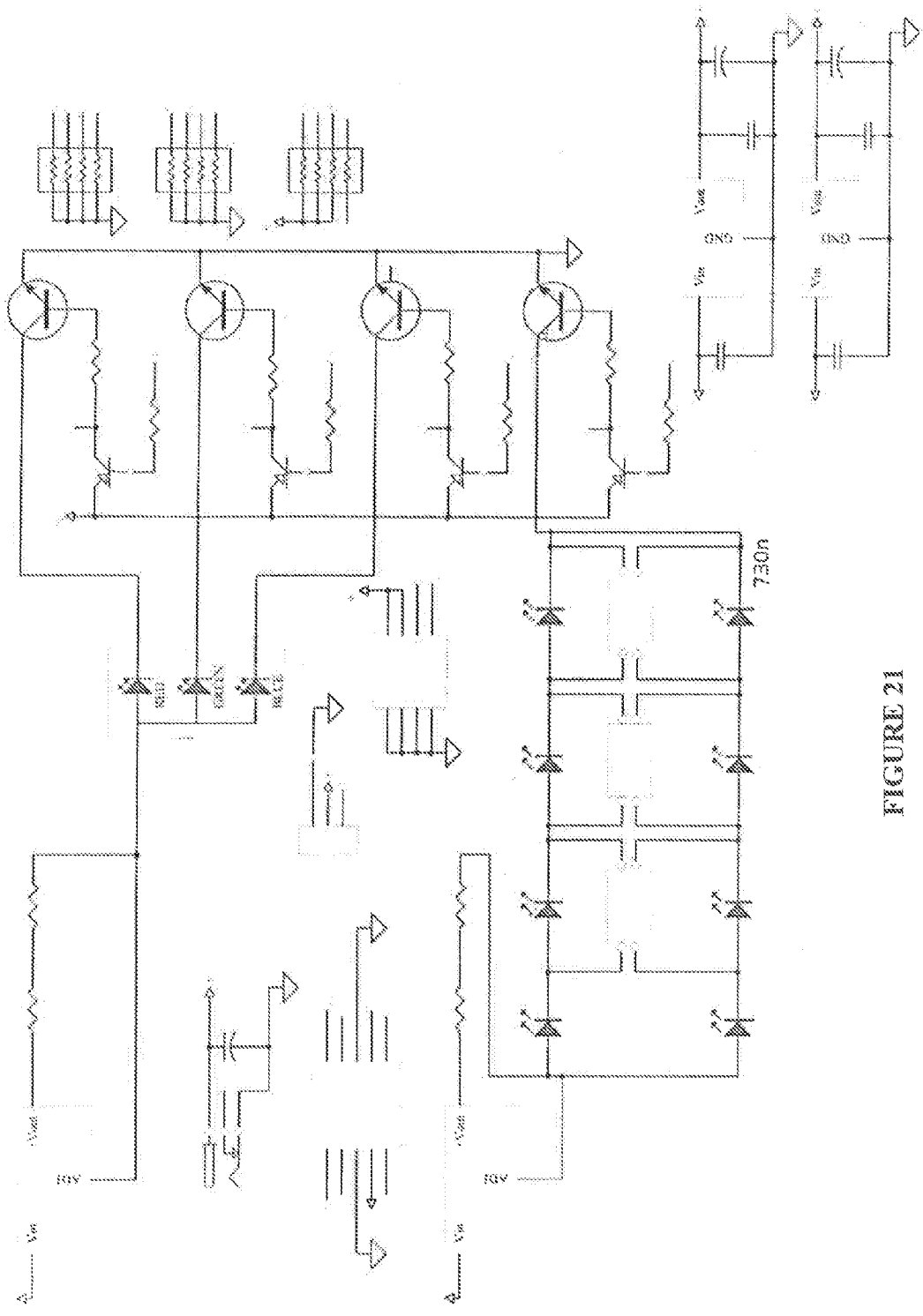
FIG. 21 is a schematic of a fourth embodiment of the invention.

FIG. 21 illustrates a circuit diagram of a fourth example of the invention comprising an array of 8 LEDs at 730 nm.

Figure 22:
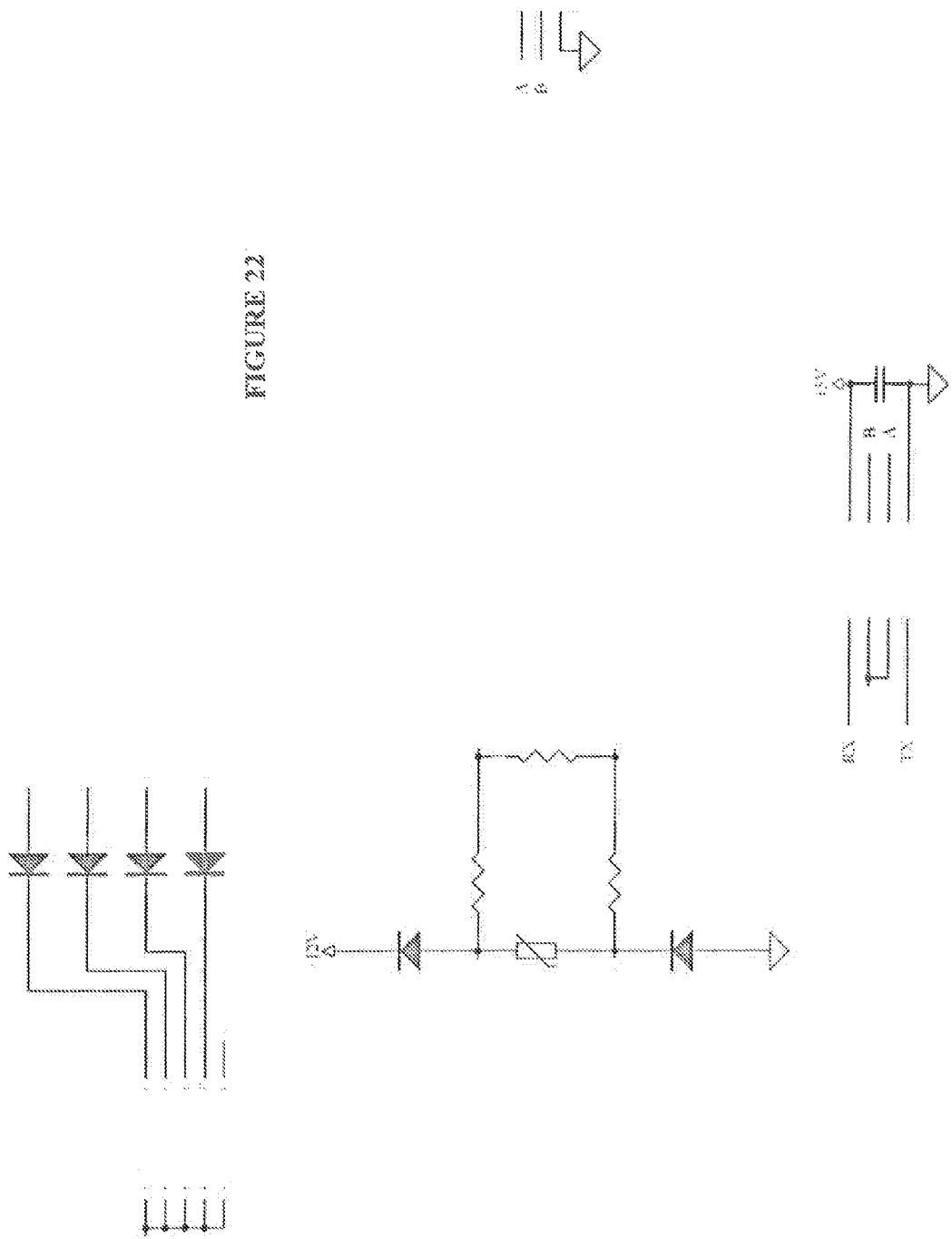
FIG. 22 is a schematic of a communication option for the fourth embodiment.

FIG. 22 illustrates a communication option for the embodiment shown in FIG. 21.

Figure 23:
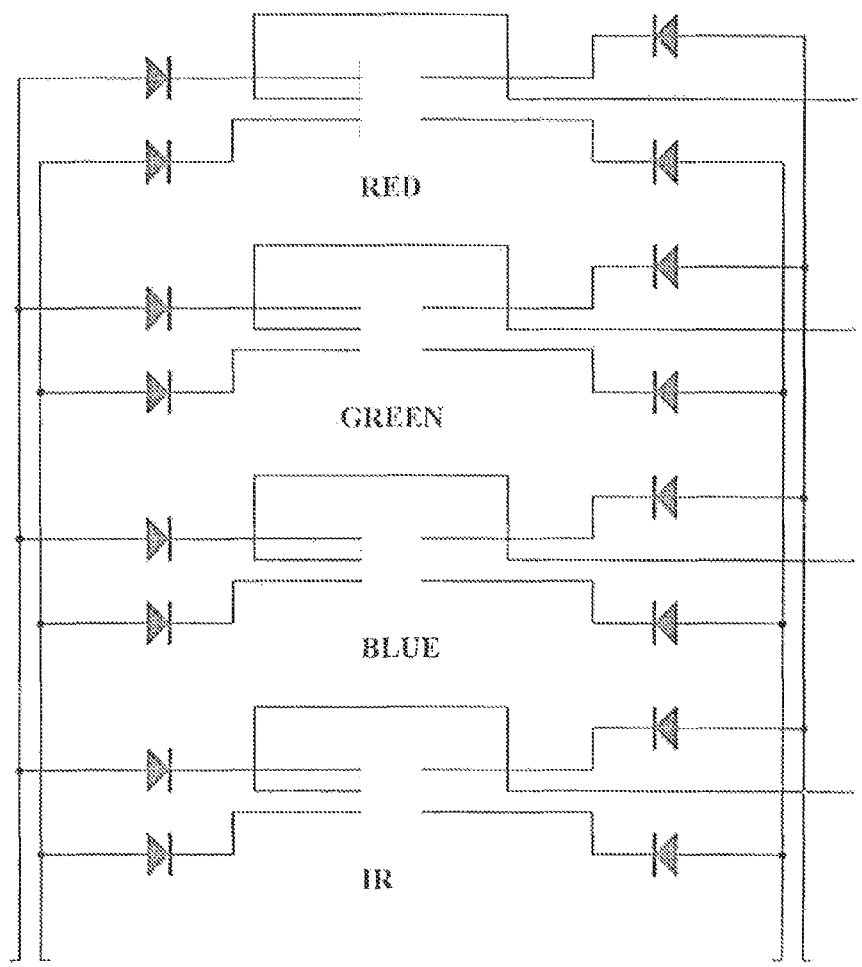
FIG. 23 is a schematic of a switch option for the fourth embodiment of the invention.

FIG. 23 illustrates a switch option for the embodiment shown in FIG. 21.

What is claimed is:

1. An apparatus for metabolism manipulation of life forms using spectral output comprising:
    at least one array of diffuse LED light sources, having a predetermined number of metabolic manipulating spectral emissions, for sending one or more environmental signals selected from the group consisting of: day/night cycles, seasonal cycles, competitive signals and harsh condition preparedness, so that said predetermined number of metabolic manipulating spectral emissions is compatible with at least one photosensitive characteristic of the life forms for manipulating a metabolic process thereof;
    a remotely programmable microcontroller, for controlling said spectral emissions in a desired manner, operatively connected to said at least one array, by selectively sending on commands, off commands and intensity commands to said at least one array,
    software for driving said microcontroller,
    a memory for storing said software,
    a power source operatively connected to the at least one array of diffuse LED light sources, and
    a graphic user interface for an operator input to said apparatus.

2. The apparatus of claim 1, wherein said life forms are plants and said at least one array of diffuse LED light sources has photosynthetic promoting spectral emissions.

3. The apparatus of claim 2 wherein said at least one array of LED light sources comprises a first plurality of identical diffuse LED light sources having a first spectral emission, a second plurality of identical diffuse LED light sources having a second spectral emission and a third plurality of identical diffuse LED light sources having a third spectral emission, and each of the first second and third pluralities of identical diffuse LED light sources are controlled by the microcontroller.

4. The apparatus of claim 3 wherein said first, second and third pluralities of diffuse LED light sources populate a respective first, second and third distinct surface areas of the at least one array.

5. The apparatus of claim 3 wherein the first, second and third pluralities of diffuse LED light sources are mixed to populate an entire surface of the at least one array.

6. The apparatus of claim 5 wherein said illumination commands include, for each of the first, second and third pluralities of diffuse LED light sources, on commands, off commands, intensity commands and strobe commands.

7. The apparatus of claim 6 wherein said strobe commands activate the lights at a strobe frequency of 36 KHz.

8. The apparatus of claim 3 wherein said first, second and third spectral emissions are at respective first, second and third photosynthetic promoting wavelengths.

9. The apparatus of claim 2 wherein the at least one array of LED light sources and the micro-controller is fixed to a single circuit board.

10. The apparatus of claim 1, wherein said life forms are plants having photosynthetic characteristics.

11. The apparatus of claim 1 wherein the microcontroller is adapted to transmit illumination commands to the at least one array of LED light sources.

12. The apparatus of claim 1, wherein said life forms are multi-cellular animals which utilize photometric environmental signals.

13. The apparatus of claim 1 wherein the commands further include pre-glow and afterglow commands.

14. The apparatus of claim 1 wherein the microcontroller is programmed to command the at least one array to emit predetermined wavelengths of photosynthetic promoting light for a first predetermined period of time.

15. The apparatus of claim 14, wherein the microcontroller is programmed to command the at least one array to emit predetermined wavelengths of predetermined power outputs for a second predetermined period of time.

16. The apparatus of claim 1 wherein the at least one array of diffuse LED light sources is networked to another at least one array of LED light sources to form a networked array and the networked array is controlled by a control means.

17. The apparatus of claim 1 wherein the at least one array of diffuse LED light sources is programmable remotely, over the Internet, via a handheld device.

18. The apparatus of claim 1 wherein the at least one array of diffuse LED light sources comprises a predetermined number of pluralities of identical diffuse LED light sources having a predetermined number of respective photosynthetic promoting spectral emissions so that said predetermined number of respective photo-synthetic promoting spectral emissions is compatible with the photosynthetic characteristics of a plant of interest and sufficient to promote growth thereof.

19. The apparatus of claim 1, wherein said software is open source software.

20. A method for plant metabolism manipulation using spectral output comprising the steps of:
    a. Determining a metabolic light sensitivity of a plant of interest;
    b. Fabricating an array of light sources comprising in combination desired pluralities of diffuse LED light sources having desired spectral emissions that are compatible with said metabolic light sensitivity of said plant of interest;
    c. Placing the plant of interest in desirable proximity to said array of light sources; and,
    d. Operatively connecting a programmable microprocessor to the array of light sources
    wherein the programmable microprocessor is adapted to transmit on commands, off commands, and intensity commands to the desired pluralities of diffuse LED light sources so that the desired pluralities of diffuse LED light sources emit the desired spectral emissions at a desired time and for a desired period at a desired intensity to imitate daylight including a predawn glow, a sunlight cycle and an after sunset glow, the programmable microprocessor controlling spectral emissions to manipulate plant metabolism to achieve at least one of forcing flowering, manipulating inter-nodal distances, and driving root propagation; and
    at least one array of diffuse LED light sources comprises a predetermined number of pluralities of identical diffuse LED light sources having a predetermined number of respective photosynthetic promoting spectral emissions so that said predetermined number of respective photo-synthetic promoting spectral emissions is compatible with the photosynthetic characteristics of said plant of interest and sufficient to promote growth thereof.

21. The method of claim 20 further including the step of strobing specific pluralities of light sources for desired time intervals at desired intensities.

22. The method of claim 20, wherein there is more than one array of diffuse light sources including, in addition to the array of diffuse light sources with spectral emissions that are compatible with said photosynthetic properties of said plant, an array of diffuse light sources providing one or more of the following environmental signals selected from: seasonal cycles, competitive signals and harsh condition preparedness.

23. The method of claim 20 further comprising:
implementing a Phototropic Morphosis Management System (PMMS) methodology;
gathering data regarding phototropic signalling and photosynthesis manipulations for said plant of interest; and
utilizing said Phototropic Morphosis Management System to optimize said a predetermined number of pluralities of identical diffuse LED light sources for said plant of interest.

24. A method for plant metabolism manipulation using spectral output comprising the steps of:
a. Determining the metabolic light sensitivity of an invasive plant of interest;
b. Fabricating an array of light sources comprising in desired pluralities of LED light sources;
c. Placing a target area in desirable proximity to said array of light sources; and,
d. Operatively connecting a programmable microprocessor to the array of light sources,
wherein the programmable microprocessor is adapted to transmit on commands, off commands, and intensity commands to the desired pluralities of light sources so that the desired pluralities of diffuse light sources emit the desired spectral emissions at a desired time and for a desired period at a desired intensity to imitate daylight including a predawn glow, a sunlight cycle and an after sunset glow, and the programmable microprocessor controlling spectral emissions to manipulate plant metabolism for the purpose of inhibiting growth of the invasive plant in the target area; and
at least one array of diffuse LED light sources comprises a predetermined number of pluralities of identical diffuse LED light sources having a predetermined number of respective photosynthetic promoting spectral emissions so that said predetermined number of respective photosynthetic promoting spectral emissions is compatible with the photosynthetic characteristics of said plant of interest and sufficient to promote growth thereof.

* * * * *